US007498138B2

(12) United States Patent
Zhang et al.

(10) Patent No.: US 7,498,138 B2
(45) Date of Patent: Mar. 3, 2009

(54) MULTIMERIZATION OF HIV-1 VIF PROTEIN AS A THERAPEUTIC TARGET

(75) Inventors: Hui Zhang, Philadelphia, PA (US); Roger J. Pomerantz, Chalfont, PA (US); Bin Yang, Bala Cynwyd, PA (US)

(73) Assignee: Thomas Jefferson University, Philadelphia, PA (US)

( * ) Notice: Subject to any disclaimer, the term of this patent is extended or adjusted under 35 U.S.C. 154(b) by 88 days.

(21) Appl. No.: 11/809,953

(22) Filed: Jun. 4, 2007

(65) Prior Publication Data

US 2008/0167199 A1 Jul. 10, 2008

Related U.S. Application Data

(62) Division of application No. 10/688,100, filed on Oct. 17, 2003, now Pat. No. 7,226,741, which is a division of application No. 10/118,575, filed on Apr. 8, 2002, now Pat. No. 6,653,443.

(60) Provisional application No. 60/282,270, filed on Apr. 6, 2001.

(51) Int. Cl.
*C12Q 1/68* (2006.01)
(52) U.S. Cl. .......................... 435/6; 435/91.1
(58) Field of Classification Search ............... 435/6, 435/91.1
See application file for complete search history.

(56) References Cited

FOREIGN PATENT DOCUMENTS

| EP | 0330359 A2 | 8/1989 |
|----|-----------|--------|
| EP | 0959136 A1 | 11/1999 |
| WO | WO 95/05851 A1 | 3/1995 |
| WO | WO 98/52970 A1 | 11/1998 |
| WO | WO 02/081504 A3 | 10/2002 |

OTHER PUBLICATIONS

Choppin J et al.: "Analysis of Physical Interactions between Peptides and HLA Molecules and Application to the Detection of Human Immunodeficiency Virus 1 Antigenic Peptides", Journal of Experimental Medicine, vol. 172, Sep. 1990, pp. 889-899.
Friedler et al.: "Peptides Derived from HIV-1 Vif: A Non-substrate Based Novel Type of HIV-1 Protease Inhibitors", Journal of Molecular Biology, vol. 287, 1999, pp. 93-101.
Jin X et al.: "Identification of Subdominant Cytotocis T Lymphocyte Epiptopes Encoded by Autologous HIV Type 1 Sequences, Using Dendritic Cell Stimulation and Computer-Driven Algorithm" AIDS Research and Human Retroviruses, vol. 16, No. 1, Jan. 2000.
Yang S et al.: "The Multimerization of Human Immunodeficiency Virus Type I Vif Protein", The Journal of Biological Chemistry, vol. 276, No. 7, Nov. 8, 2000, pp. 4889-4893.
Zhang, Hui et al.: "Human Immunodeficiency Virus Type 1 Vif Proteins Is an Integral Component of an MrNP Complex of Viral RNA and Could Be Involved in the Viral RNA Folding and Packaging Process", Journal of Virology, Sep. 2000, p. 8252-8261.
Guy et al.: "A specific inhibitor of cysteine proteases impairs a Vif-dependent modification of human immunodeficiency virus type 1 Env protein", Journal of Virology, vol. 65, No. 3 (Mar. 1991), pp. 1325-1331 (abstract only).
Yang, et al.: "Mitogen-activated Protein Kinase Phosphorylates and Regulates the HIV-1 Vif Protein", *The Journal of Biological Chemistry*, vol. 273, No. 45, Issue of Nov. 6, 1998 pp. 29879-29887.
Huvent, Isabelle, et al.: "Interaction and co-encapsidation of human immunodeficiency virus type 1 Gag and Vif recombinant proteins" *Journal of General Virology*, vol. 79, pp. 1069-1081 (1998).
Goncalves, Joao, et al.: "Biological Activity of Human Immunodeficiency Virus Type 1 Vif Requires Membrane Targeting by C-Terminal Basic Domains", *Journal of Virology*, vol. 69, No. 11, Nov. 1995, pp. 7196-7204.
Bouyac, Michele, et al.: "Human Immunodeficiency Virus Type 1 Vif Protein Binds to the Pr55$^{Gag}$ Precursor", *Journal of Virology*, vol. 71, No. 12, Dec. 1997, pp. 9358-9365.
Gabuzda, Dana H., et al.: "Rolf of *vif* in Replication of Human Immunodeficiency Virus Type 1 in CD4$^+$ T Lymphocytes", *Journal of Virology*, vol. 66, No. 11, Nov. 1992, pp. 6489-6495.
Khan, Mohammad A., et al.: "Human Immunodeficiency Virus Type 1 Vif Protein is Packaged into the Nucleoprotein Complex through an Interaction with Viral Genomic RNA", *Journal of Virology*, vol. 75, No. 16, Aug. 2001, pp. 7252-7265.
Simon, James H. M., et al.: "Mutational Analysis of the Human Immunodeficiency Virus Type 1 Vif Protein", *Journal of Virology*, vol. 73, No. 4, Apr. 1999, pp. 2675-2681.

*Primary Examiner*—Ali R. Salimi
(74) *Attorney, Agent, or Firm*—Drinker Biddle & Reath LLP; Daniel A. Monaco

(57) ABSTRACT

The HIV-1 protein Vif comprises a multimerization domain that allows Vif-Vif interaction and Vif multimerization, which is important for Vif function in the HIV-1 life-cycle. A method for screening for an antagonist of Vif comprises contacting the multimerization domain of Vif with a test compound that specifically binds the multimerization domain. Antagonists identified by the screening assay inhibit Vif multimerization. The antagonists inhibit essential functions of Vif and accordingly are useful as inhibitors of HIV-1 replication.

17 Claims, 9 Drawing Sheets

SEQUENCE LISTING

<160> NUMBER OF SEQ ID NOS: 26

<210> SEQ ID NO 1
<211> LENGTH: 14
<212> TYPE: PRT
<213> ORGANISM: Artificial Sequence
<220> FEATURE:
<223> OTHER INFORMATION: Fragment of vif protein sequence

<400> SEQUENCE: 1

Ala Ala Leu Ile Lys Pro Lys Gln Ile Lys Pro Pro Leu Pro
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Fragment of vif protein sequence

<400> SEQUENCE: 2

Asp Tyr Lys Asp Asp Asp Asp Lys
1               5

```
<210> SEQ ID NO 3
<211> LENGTH: 10
<212> TYPE: PRT
<213> ORGANISM: Artificial Sequence
<220> FEATURE:
<223> OTHER INFORMATION: Fragment of c-Myc protein sequence

<400> SEQUENCE: 3

Glu Gln Lys Leu Ile Ser Glu Glu Asp Leu
 1               5                  10

<210> SEQ ID NO 4
<211> LENGTH: 7
<212> TYPE: PRT
<213> ORGANISM: Artificial Sequence
<220> FEATURE:
<223> OTHER INFORMATION: Fragment of vif protein sequence

<400> SEQUENCE: 4

Ser Leu Gln Tyr Leu Ala Leu
 1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 5

Ser Asn Phe Ala Ser Ile Thr Thr Pro Arg Pro His
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 6

Trp Pro Thr Asn Pro Thr Thr Val Pro Val Pro Ser
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 7

Leu Thr Ser Asp Thr Tyr Phe Leu Pro Val Pro Ala
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 8

Ser Leu His Trp Pro Val Ser His Pro Pro Pro Pro
 1               5                  10
```

```
<210> SEQ ID NO 9
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 9

Ser Val Ser Val Gly Met Lys Pro Ser Pro Arg Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 10

Trp His Ser Gln Arg Leu Ser Pro Val Pro Pro Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 11

Ser Asn Gln Gly Gly Ser Pro Leu Pro Arg Ser Val
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 12

Ser Glu Pro His Leu Pro Phe Pro Val Leu Pro His
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 13

Leu Pro Leu Pro Ala Pro Ser Phe His Arg Thr Thr
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 14

Tyr Pro Leu Pro His Pro Met Trp Ser Met Leu Pro
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 15

Thr Met Thr Pro Pro Thr Ser Val Arg Gly Thr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 16

Thr Pro Leu Pro Thr Ile Arg Gly Asp Thr Gly Thr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 17

Gly Pro Pro Pro His His Arg Asp Tyr His Gly Pro
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 18

Tyr Pro Ala Pro Ile Lys Val Leu Leu Pro Asn Ser
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 19

Ser Pro Tyr Pro Met Ala Leu Phe Pro Leu His Asn
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic peptide containing PXP motif

<400> SEQUENCE: 20

Ser Pro Tyr Pro Ser Trp Ser Thr Pro Ala Gly Arg
1               5                   10

<210> SEQ ID NO 21
```

```
<211> LENGTH: 12
<212> TYPE: PRT
<213> ORGANISM: Artificial Sequence
<220> FEATURE:
<223> OTHER INFORMATION: Fragment of vif

<400> SEQUENCE: 21

Lys Pro Lys Lys Ile Lys Pro Pro Leu Pro Ser Val
 1               5                  10

<210> SEQ ID NO 22
<211> LENGTH: 15
<212> TYPE: PRT
<213> ORGANISM: Artificial Sequence
<220> FEATURE:
<223> OTHER INFORMATION: Fragment of vif

<400> SEQUENCE: 22

Pro Pro Leu Pro Ser Val Thr Lys Leu Thr Glu Asp Arg Trp Asn
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Fragment of vif

<400> SEQUENCE: 23

Lys Lys Ile Lys Pro Pro Leu Pro Ser Val Thr Lys Leu Thr Glu
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Fragment of vif

<400> SEQUENCE: 24

Glu Ser Ala Ile Arg Lys Ala Ile Leu Gly His Ile Val Ser Pro
 1               5                  10                  15

<210> SEQ ID NO 25
<211> LENGTH: 4
<212> TYPE: PRT
<213> ORGANISM: Artificial Sequence
<220> FEATURE:
<223> OTHER INFORMATION: Fragment of vif protein

<400> SEQUENCE: 25

Pro Pro Leu Pro
 1

<210> SEQ ID NO 26
<211> LENGTH: 31
<212> TYPE: PRT
<213> ORGANISM: Artificial Sequence
<220> FEATURE:
<223> OTHER INFORMATION: Fragment of vif protein

<400> SEQUENCE: 26

Lys Val Gly Ser Leu Gln Tyr Leu Ala Leu Ala Ala Leu Ile Thr Pro
 1               5                  10                  15

Lys Lys Ile Lys Pro Pro Leu Pro Ser Val Thr Lys Leu Thr Glu
             20                  25                  30
```

MULTIMERIZATION OF HIV-1 VIF PROTEIN AS A THERAPEUTIC TARGET

CONTINUING APPLICATION DATA

This application is a divisional of U.S. application Ser. No. 10/688,100, filed Oct. 17, 2003, which is a divisional of U.S. application Ser. No. 10/118,575, filed Apr. 8, 2002 which claims priority to U.S. provisional application No. 60/282,270, filed Apr. 6, 2001.

FIELD OF THE INVENTION

The present invention generally related to the fields of molecular biology and virology and to a method for treating an individual exposed to or infected with human immunodeficiency virus type 1 (HIV-1) and, more particularly, to compositions that inhibit or prevent the replicative and other essential functions of HIV-1 viral infectivity factor protein (Vif) by interactively blocking the Vif multimerization domain.

BACKGROUND OF THE INVENTION

One approach to treating individuals infected with HIV-1 is to administer to such individuals compounds that directly intervene in and interfere with the machinery by which HIV-1 replicates itself within human cells. Lentiviruses such as HIV-1 encode a number of accessory genes in addition to the structural gag, pol, and env genes that are expressed by all replication-competent retroviruses. One of these accessory genes, vif (viral infectivity factor), is expressed by all known lentiviruses except equine infectious anemia virus. Vif protein of HIV-1 is a highly basic, 23-kDa protein composed of 192 amino acids. Sequence analysis of viral DNA from HIV-1-infected-individuals has revealed that the open reading frame of Vif remains intact. (Sova, P., et al., *J. Virol.* 96:2557-2564, 1995; Wieland, U., et al., *Virology* 203:43-51, 1994; Wieland, U., et al., *J. Gen. Virol.* 78:393-400, 1997). Deletion of the vif gene dramatically decreases the replication of simian immunodeficiency virus (SIV) in macaques and HIV-1 replication in SCID-hu mice (Aldrovandi, G. M. & Zack, J. A., *J. Virol.* 70:1505-1511, 1996; Desrosiers, R. C., et al., *J. Virol.* 72:1431-1437, 1998), indicating that the vif gene is essential for the pathogenic replication of lentiviruses in vivo.

In cell culture systems, vif-deficient (vif⁻) HIV-1 is incapable of establishing infection in certain cells, such as H9 T cells, peripheral blood mononuclear cells, and monocyte-derived macrophages. This has led to classification of these cells as nonpermissive. However, in some cells, such as C8166, Jurkat, SupT1, and HeLa-T4 cells, the vif gene is not required; these cells have been classified as permissive. (Gabuzda, D. H., et al., *J. Virol.* 66(11):6489-95, 1992; von Schwedler, U., et al., *J. Virol.* 67(8):4945-55, 1993; Gabuzda, D. H., et al., *J. AIDS* 7(9):908-15, 1994).

As Vif is required by nonpermissive but not permissive cells for HIV-1 replication two possibilities exist. In permissive cells, there may be a Vif cellular homologue that can replace Vif function in the virus-producing cells; alternatively, there may be an inhibitor(s) of viral replication in nonpermissive cells that requires Vif to counteract its effect. (Trono, D., *Cell* 82:189-192, 1995). Recently, it was proposed that Vif protein is required to counteract an unknown endogenous inhibitor(s) in the virus-producing cells. (Madani, N., & Kabat, D., *J. Virol.* 72:10251-10255, 1998; Simon, J. H., et al., *Nat. Med.* 4:1397-1400, 1998). HIV-1 Vif can complement the function of HIV-1 Vif and $SIV_{AGM}$ Vif in human nonpermissive cells, whereas it cannot complement the function of HIV-1 and $SIV_{AGM}$ Vif in simian cells. $SIV_{AGM}$ Vif, however, can complement the function of HIV-1 Vif and $SIV_{AGM}$ Vif in simian cells but not the function of HIV-1 and $SIV_{AGM}$ Vif in human cells, indicating that a cellular cofactor(s) is involved in the action of Vif protein. (Simon, J. H., et al., *EMBO J.* 17:1259-1267, 1998). Conversely, since a Vif mutant (Vif from HIV-$1_{F12}$) can inhibit wild-type HIV-1 replication in permissive cells, a Vif homologue in the permissive cells may exist. (D'Aloja, P., et al., *J. Virol.* 72:4308-4319, 1998).

It has been proposed that Vif functions in virus-producing cells or cell-free virions and affects viral assembly. (Blanc, D., et al., *Virology* 193:186-192, 1993; Gabuzda, D. H., et al., *J. Virol.* 66:6489-6495, 1992; von Schwedler, U., et al., *J. Virol.* 67:4945-4955, 1993). Defects of the vif gene do not have detectable effects on viral transcription and translation or on virion production. HIV-1 variants with a defective vif gene are able to bind and penetrate target cells but are not able to complete intracellular reverse transcription and endogenous reverse transcription (ERT) in cell-free virions. (Courcoul, M., et al., *J. Virol.* 69:2068-2074, 1995; Goncalves, J., et al., *J. Virol.* 70:8701-8709, 1996; Sova, P., & Volsky, D. J., *J. Virol.* 67:6322-6326, 1993; von Schwedler, U., et al., *J. Virol.* 67:4945-4955, 1993). When ERT is driven by the addition of deoxyribonucleoside triphophates (dNTP) at high concentrations, certain levels of plus-strand viral DNA can be completed. Moreover, when vif⁻ viruses, generated from nonpermissive cells and harboring larger quantities of viral DNA generated by ERT, are allowed to infect permissive cells, they can partially bypass the block at intracellular reverse transcription through which vif⁻ viruses without deoxynucleoside triphosphate treatment can not pass. Consequently, viral infectivity can be partially rescued from the vif⁻ phenotype. (Dornadula, G., et al., *J. Virol.* 74:2594-2602, 2000).

The expression of viral components, including viral proteins and nucleic acids, is not altered in the virions produced from nonpermissive cells. (Fouchier, R. A., et al., *J. Virol.* 70:8263-8269, 1996; Gabuzda, D. H., et al., *J. Virol.* 66:6489-6495, 1992; von Schwedler, U., et al., *J. Virol.* 67:4945-4955, 1993). Deletion of the vif gene, however, results in alterations of virion morphology. (Borman, A. M., et al., *J. Virol.* 69:2058-2067, 1995; Bouyac, M., et al., *J. Virol* 71:2473-2477, 1997; Hoglund, S., et al., *Virology* 201:349-355, 1994). The quantity of Vif protein in the HIV-1 virions generated from chronically infected cells is approximately 7 to 28 molecules per virion. (Camaur, D., & Trono, D., *J. Virol.* 70:6106-6111, 1996; Fouchier, R. A., et al., *J. Virol.* 70:8263-8269, 1996; Simon, J. H., et al., *Virology* 248:182-187, 1998). As the virion-associated Vif proteins do not depend on the expression of viral components and the amount of Vif in the virus-producing cells, it seems that Vif proteins are not specifically incorporated into the virions. (Camaur, D., & Trono, D., *J. Virol* 70:6106-6111, 1996; Simon, J. H., et al., *Virology* 248:182-187, 1998).

Although, it seems that Vif is not specifically incorporated into virions, Vif is able to bind to the NCp7 domain of p55 Gag precursors through its positively charged amino-acid enriched C-terminus. (Bouyac, M., et al., *J. Virol.* 71:9358-9365, 1997; Huvent, I., et al., *J. Gen. Virol.* 79:1069-1081, 1998). Vif protein is found to co-localize with Gag precursors in the cytoplasm of HIV-1-infected cells. (Simon, J. H., et al., *J. Virol.* 71:5259-5267, 1997). The molar ration of Vif to Gag precursors in infected cells is 1:1.7, suggesting that Vif plays a structural rather than a regulatory role in virus-producing cells. (Goncalves, J., et al., *J. Virol.* 68:704-712, 1994; Simon, J. H., et al., *Virology* 248:182-187, 1998).

Vif has been shown to be an RNA-binding protein and an integral component of a messenger ribonucleoprotein (mRNP) complex of viral RNA in the cytoplasm of HIV-1-infected cells. The expression of Vif in infected cells is quite high, and the majority of Vif in virus-producing cells is in the cytoplasmic fraction; some is associated with the cellular membrane. The Vif protein in this mRNP complex may protect viral RNA from various endogenous inhibitors and could mediate viral RNA engagement with HIV-1 Gag precursors and thus could be involved in genomic RNA folding and packaging. As such, the interaction between Vif and HIV-1 RNA plays an important role in the late events of the HIV-1 life cycle. Given the Vif protein's direct or indirect involvement in the viral assembly process, it is an ideal target for anti-HIV-1 therapeutics.

Many HIV-1 proteins, including Gag, protease, reverse transcriptase, integrase, glycoprotein 41(gp41), Tat, Rev, Vpr, and Nef, have been shown to form dimers or multimers in vitro and in vivo. The formation of dimers or multimers has been demonstrated to be important for their functions in the lentiviral life-cycle. (Frankel, A. D. & Young, J. A., *Ann. Rev. Biochem.* 67:1-25, 1998; Vaishnav, Y. N. & Wong-Staal, F., *Annu Rev Biochem* 60:577-630, 1991; Zhao, L. J., et al., *J Biol Chem* 269(51):32131-7, 1994; Liu, L., et al., *J. Virol.* 74:5310-5319, 2000). The present invention provides evidence that Vif protein possesses a strong tendency to self-associate and that multimerization of Vif proteins is important for Vif function in the viral life-cycle. The present invention is directed to a method of treating HIV-1 exposed or infected individuals by administering a composition that inhibits or prevents the replicative and other essential functions of Vif by binding to, or otherwise associating with, the multimerization domain of Vif, thereby preventing multimerization of Vif and, consequently, HIV-1 replication.

ABBREVIATIONS

"HIV-1" means "human immunodeficiency virus type I."
"Vif" means "virion infectivity factor."
"GST" means "glutathione-S-transferease."
"CAT" means "chloramphenicol acetyltransferase."
"IP" means "immunoprecipitation."
"WB" means "Western blotting."

DEFINITIONS

The term "antagonist" as used herein, refers to a molecule that binds to Vif protein, preferably, the multimerization domain within Vif protein, thereby inhibiting Vif-Vif interaction and Vif protein multimerization. Antagonists may include proteins or peptidomimetics thereof, nucleic acids, carbohydrates, or any other molecules, which inhibits Vif protein multimerization.

The terms "analogs," "derivatives," or "fragments" are used interchangeably to mean a chemical substance that is related structurally and functionally to another substance. An analog, derivative, or fragment contains a modified structure from the parent substance, in this case Vif protein, and maintains the function of the parent substance, in this instance, the binding ability to the multimerization domain of Vif protein in cellular and animal models. The biological activity of the analog, derivative, or fragment may include an improved desired activity or a decreased undesirable activity. The analogs, derivatives or fragments may be prepared by various methods known in the art, including but not limited to, chemical synthesis or recombinant expression. Analogs, derivatives, or fragments of the instant invention, include, but are not limited to, synthetic or recombinant peptides that are homologous to Vif protein or fragment thereof (consisting of at least the sequence from amino acid residue 144-171, preferably, 151-164, more preferably, 161-164).

Figure 1A:
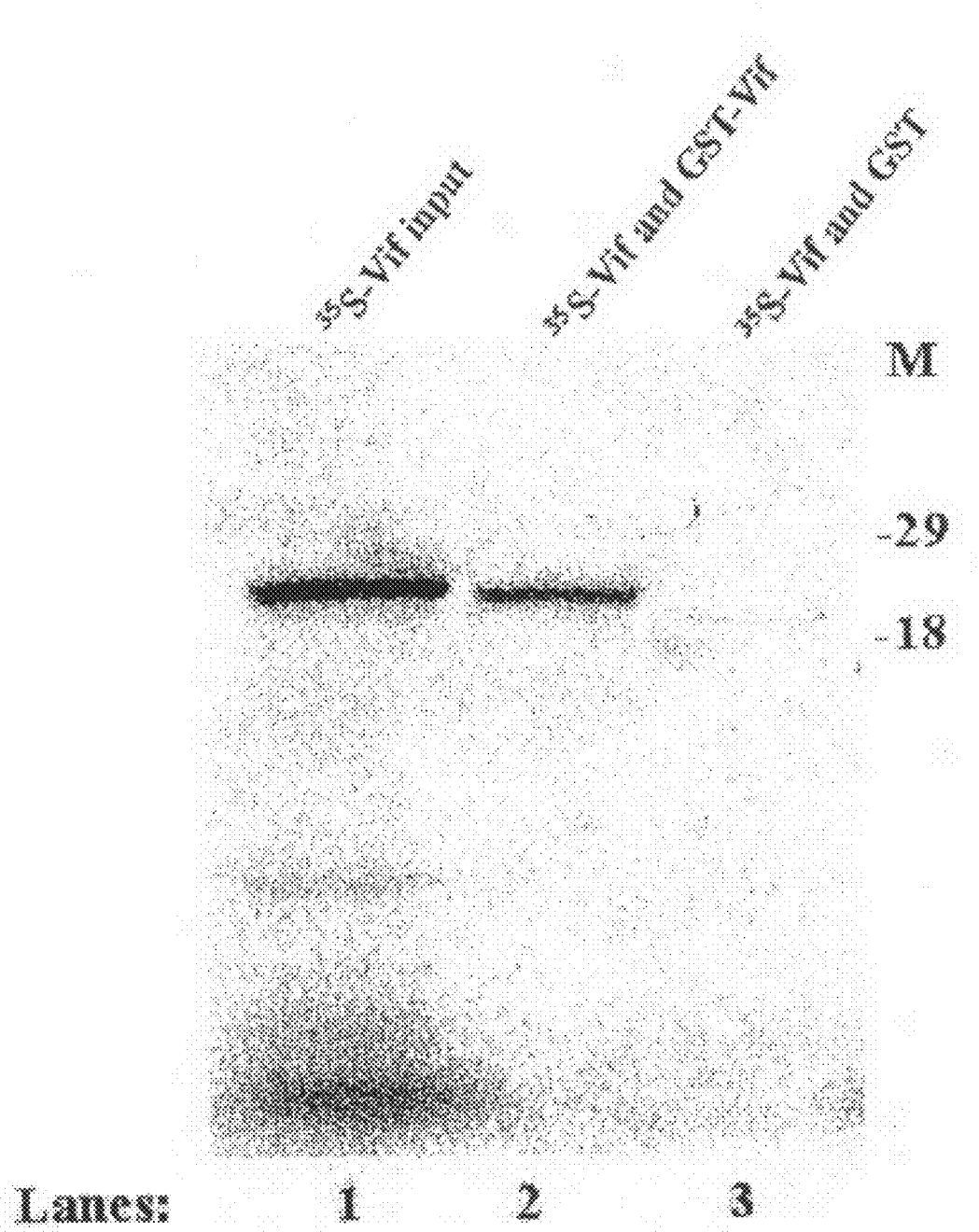
FIG. 1. Vif Self Association in a Cell-free System.

A. An autoradiograph illustrating that GST-Vif (lane 2) but not GST (lane 3) can bind to in vitro translated $^{35}$S-labeled HIV-1$_{NL4-3}$ Vif protein. $^{35}$S-labeled HIV-1$_{NL4-3}$ Vif proteins were allowed to bind with GST-Vif conjugated beads. After binding, the bead associated $^{35}$S-labeled Vif was analyzed via SDS-PAGE and direct autoradiography.

B. An autoradiograph showing that under native or relatively native conditions $^{35}$S-labeled HIV-1$_{NL4-3}$ Vif proteins form monomers, dimers, trimers or tetramers. In vitro translated $^{35}$S-labeled HIV-1$_{NL4-3}$ Vif proteins were loaded directly onto a 4-20% Tris-HCl gel (SDS-free) with native loading buffer [62.5 mM Tris-HCl (pH 6.8) and 20% glycerol] plus SDS at different concentrations. Electrophoresis was performed with a Tris-Glycine running buffer containing 0.05% SDS, followed by autoradiography.

FIG. 2. The Effect of Vif Mutants on Vif-Vif Interactions.

A. A schematic showing a series of deletions along the Vif protein generated using PCR-based mutagenesis and in vitro translation. The in vitro translated $^{35}$S-labeled HIV-1$_{NL4-3}$ Vif protein and its mutants were allowed to bind to GST-Vif conjugated on agarose beads. The bead-associated, $^{35}$S-labeled Vif protein and its mutants were subjected to SDS-PAGE and visualized by direct autoradiography. The ratio of bound Vif versus the input were calculated using the ratio of GST-Vif bound $^{35}$S-labeled wild-type Vif protein and $^{35}$S-labeled wild-type Vif input as 100% (with the standard deviations). The values were obtained by quantitation with densitometry of the autoradiography. In most cases, the data reflect at least five independent experiments.

B. An autoradiograph illustrating that in the presence of 0.1% SDS, $^{35}$S-labeled HIV-1$_{NL4-3}$ Vif protein mutants Δ151-192 and Δ151-164 are unable to form multimers, while other mutants are able to do so. In vitro translated $^{35}$S-labeled HIV-1$_{NL4-3}$ Vif protein and its mutants (50,000 cpm count for each) were loaded directly onto a 4-20% Tris-HCl gel (SDS-free) with a loading buffer [62.5 mM Tris-HCl (pH 6.8) and 20% glycerol] plus 0.1% SDS. Electrophoresis was performed with a Tris-Glycine running buffer containing 0.05% SDS, followed by autoradiography.

Figure 3:
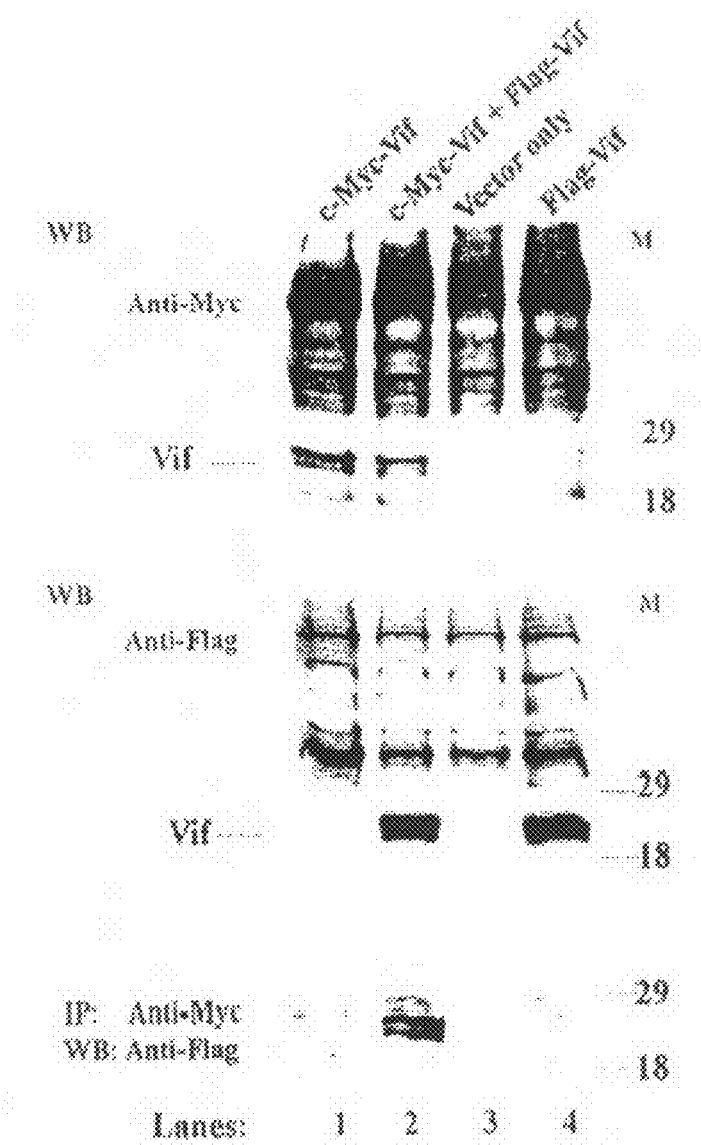

FIG. 3. Co-immunoprecipitation Method to Study Vif-Vif Interactions Within Cells.

Western Blots (top two panels) showing that the expression of Vif protein tagged with c-Myc or Flag epitope at its C-terminus in COS-1 transfected cells can be detected using A14 anti-c-Myc polyclonal antibody and or M2 anti-Flag monoclonal antibody, respectively. COS-1 cells were transfected with vectors harboring Flag or c-Myc tagged Vif. After 54 hours of incubation at 5% $CO_2$, 37° C., 20 μg total cell lysates were resolved by 15% Tris-HCl gel. A third Western Blot illustrates that Flag-tagged Vif was co-precipitated with Myc-tagged Vif when the cell lysates were immunoprecipitated with A14 anti-c-Myc polyclonal antibody. For co-immunoprecipitation, the whole cell lysates from the same batch were subjected to immunoprecipitation with A14 anti-c-Myc polyclonal antibody. Immunoprecipitates are resolved at 15%

Tris-HCl gel and transferred onto a membrane and then detected using an M2 anti-Flag antibody.

FIG. 4. Mammalian Two-hybrid System to Study Vif-Vif Interaction.

A. A schematic map showing the plasmids utilized in the experiments: pVif-VP, pGAL-Vif, and pSG5GalVP.

B. A gel illustrating the CAT activity of COS-1 cells transfected with plasmids combined with various vectors. After 48 hours, cell lysates were harvested and subjected to CAT analyses.

Figure 5:
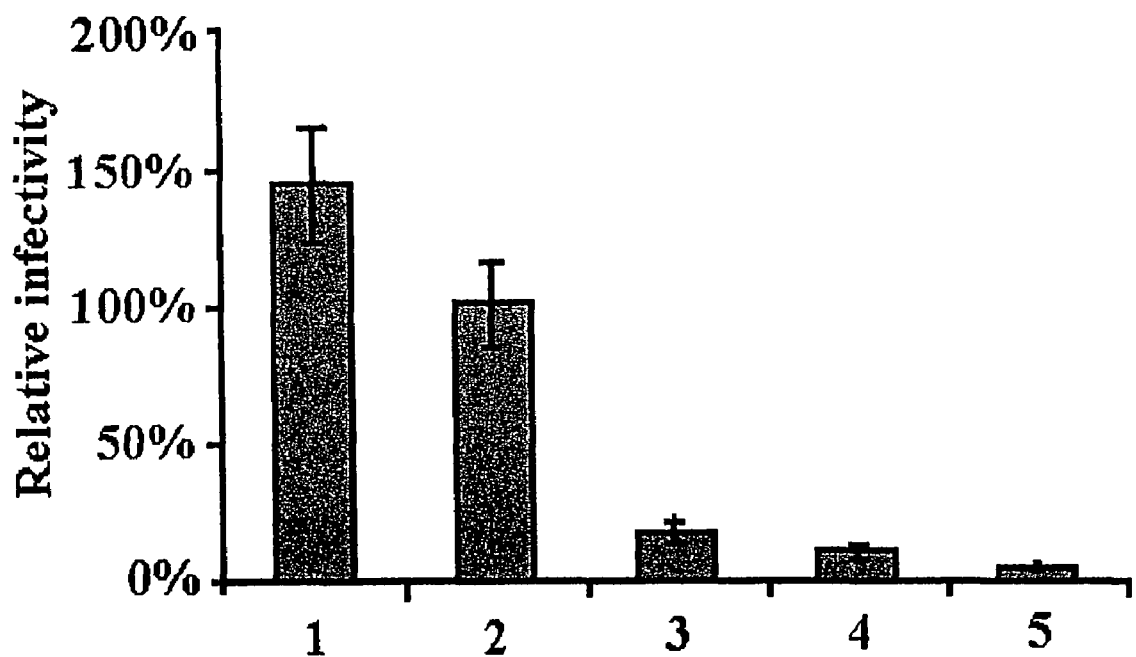

FIG. 5. Viral Infectivity Affected by Vif or Vif Mutants.

A diagram depicting the CAT activity of HelaCD4-CAT cells infected with recombinant viruses. The pCI-Neo constructs, containing wild-type vif gene or its mutants, pNL4-3ΔenvΔvif plasmid and pMD.G (containing VSV env), were co-transfected into H9 cells to generate the pseudotyped viral particles. After concentration via ultracentrifuge, the viral particles were normalized by HIV-1 p24 antigen. In the presence of polybrene (8 μg/ml), the viruses were used to infect HelaCD4-CAT cells. After 48 hours, the cell lysates were collected and subjected to CAT analyses. Lane 1) pNL4-3; Lane 2) pNL4-3ΔenvΔvif, VSV env plus wild-type vif, Lane 3) pNL4-3ΔenvΔvif, VSV env, plus vifΔ 151-164; Lane 4) pNL4-3ΔenvΔvif, VSV env, plus vifΔ 144-150; Lane 5) pNL4-3ΔenvΔvif, VSV env, plus pCI-Neo vector only. The value of wild-type vif complementation was set as 100%. The relative values of the other samples were calculated accordingly. The figure represents three independent experiments. Values are means ±standard deviations.

Figure 6:
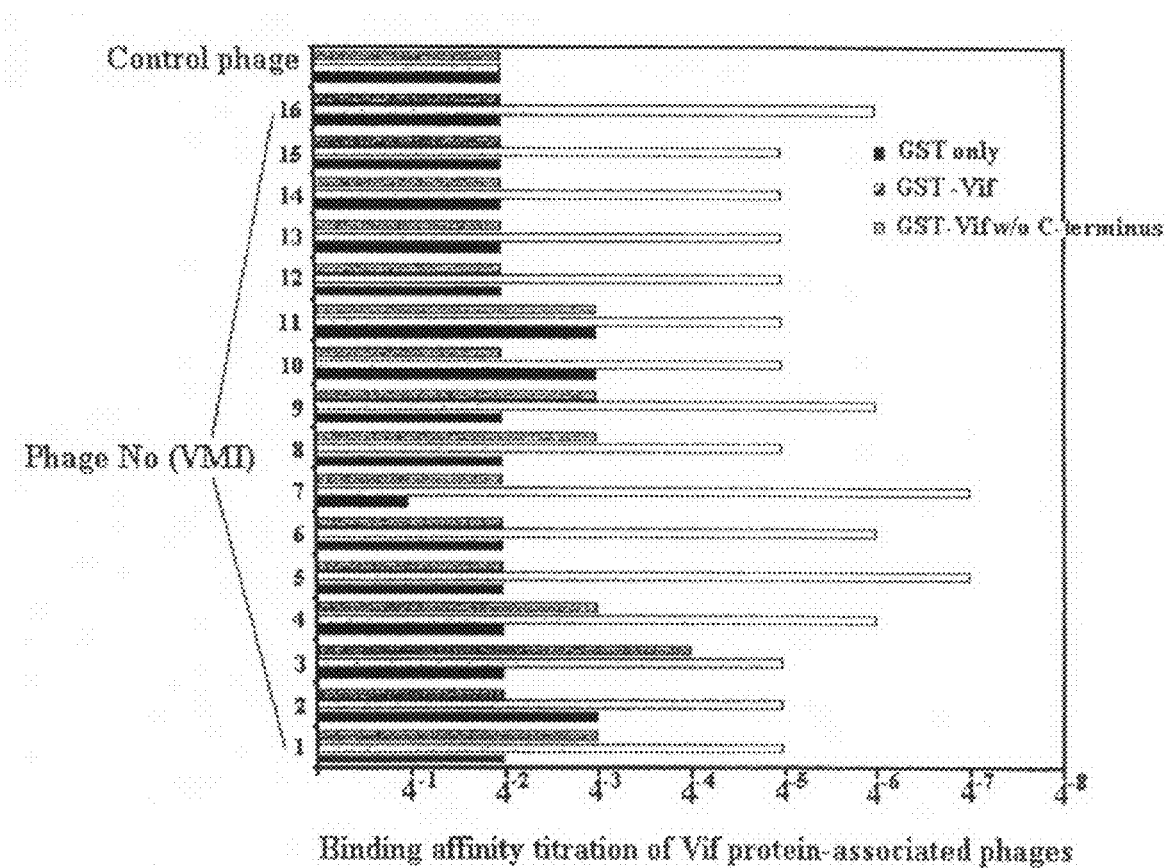

FIG. 6. The Relative Affinity Comparison between PXP Motif Containing Peptides.

The GST-Vif protein, Vif mutant (deletion of 151-192 amino acids), and GST only were placed onto the plate. The phage clones isolated through Vif-containing column were serially diluted and added. After incubation to allow phage-Vif binding, excess phages were washed off. Anti-M13 phage antibody, conjugated with HRP, was added to bind the phages that were captured by Vif. After washing, the substrate was added and color development was allowed. The phages captured by Vif, therefore, were semi-quantitated. OD at 405 nm equal or larger than 0.15 was considered as positive. The phage sample number (VMI) was the same as shown in Table 1.

DETAILED DESCRIPTION OF THE INVENTION

Vif protein of HIV-1 is essential for viral replication in vivo and productive infection of peripheral blood mononuclear cells (PBMC), macrophages and H9 T-cells. The molecular mechanism(s) of Vif remains unknown and needs to be further determined. The present invention demonstrates that like many other proteins encoded by HIV-1, Vif proteins possess a strong tendency towards self-association. Under relatively native conditions, Vif proteins form multimers in vitro, including dimers, trimers, or tetramers. In vivo binding assays, such as co-immunoprecipitation and a mammalian two-hybrid system, demonstrate that Vif proteins interact with each other within a cell, indicating that the multimerization of Vif proteins is not simply due to fortuitous aggregation.

The present invention further evidences that the domain affecting Vif self-association is located at the C-terminus of this protein, especially the proline-enriched 151-164 region. The sequence of this domain is AALIKPKQIKPPLP (SEQ. I.D. NO: 1). Studies demonstrate that a Vif mutant with deletion at amino acid positions 151-164 is unable to rescue the infectivity of vif-defective viruses generated from H9 T-cells, implying that the multimerization of Vif proteins is important for Vif function in the viral life-cycle.

Methods

Plasmid Constructions

With infectious clone pNL4-3 as a template, deletion mutants of HIV-1 Vif were generated by polymerase chain reaction (PCR)-mediated and site-directed mutagenesis. (Zhang, H., et al., *Proc. Natl. Acad. Sci. USA* 93(22):12519-24, 1996). The PCR-generated wild-type vif gene and its mutants were then inserted into pCITE-4a vector (Novagen, Madison, Wis.) for in vitro translation. The vif gene also was inserted into pGEX vector for in vitro expression and isolation of GST-Vif fusion protein. For studying intracellular Vif-Vif interaction, vif genes were tagged via PCR with Flag (DYKDDDDK) (SEQ. I.D. NO: 2) or c-Myc (EQKLISEEDL) (SEQ. I.D. NO: 3) epitope-encoding sequences at the 3' terminus respectively. These tagged vif genes were then inserted into the vector pCI-Neo, which contains a chimeric intron just downstream of the CMV enhancer and immediate early promoter (Promega, Madison, Wis.). The resulting plasmids were named pCI-vif-c-myc or pCI-vif-flag, respectively. For mammalian two-hybrid analysis, either pGal-Vif or pGal-VifΔ151-164 was constructed by replacing the Hind III-BamH I fragment (containing vp gene) of pSG5GalVP with a PCR-amplified complete vif gene or its mutant Δ151-164. The pVif-VP or pVifΔ151-164-VP was constructed by replacing the EcoRI-BglII fragment (containing gal4 gene) of pSG5GalVP with an PCR-amplified complete vif gene or its mutant Δ151-164, respectively. (Shimano, R., et al., *Biochem. Biophys. Res. Comm* 242(2):313-6, 1998). The integrity of all the constructs was confirmed by DNA sequencing.

Protein Expression and In Vitro Binding Assays

The vector pGEX, with or without the vif gene, was transformed into BL21 competent cells (Novagen, Madison, Wis.). After growth at 37° C. to approximately 0.6 O.D., the expression of GST or GST-Vif proteins was induced by 0.4 mM isopropylthio-β-D-galactoside (IPTG). The bacterial cells were lyzed by adding lysing buffer (1% Triton-X-100, 0.1 mg/ml lysozyme, 2 mM EDTA, 1 mM PMSF, 2 ug/ml leupeptin, and 1 μg/ml aprotinin), followed by sonication. The sample was pelleted at 12,000 g for 10 min at 4° C., and the supernatant was applied to a glutathione-conjugated agarose bead (Sigma, St. Louis, Mo.) column. After batch binding, the matrix was washed three times, each time by the addition of 10 bed volumes of phosphorus-buffer saline (PBS). The GST or GST-Vif conjugated agarose beads were then aliquoted and stored at −20° C. Conversely, $^{35}$S-labeled Vif or its mutant proteins were synthesized utilizing SPT3 kits (Novagen, Madison, Wis.). The protocol supplied by the manufacturer was followed. After in vitro translation, RNase A (0.2 mg/ml) was added to stop the reaction and remove tRNAs and the in vitro transcribed mRNA. The trichloroacetic acid (TCA)-insoluble radioactive amino acids were quantitated in the presence of a scintillation cocktail.

For GST pull-down assays, a GST or GST-Vif conjugated bead slurry was mixed with $^{35}$S-labeled Vif or its mutants (50,000 cpm) in a binding buffer [150 mM NaCl, 20 mM Tris-HCl (pH 7.5), 0.1% Triton-X-100]. After binding at 4° C. for 1 hour, the mixture was centrifuged at 3,000 g for 1 min, and the beads were washed three times with binding buffer. The $^{35}$S-labeled Vif proteins were dissociated from the beads by adding SDS-containing loading buffer and heating at 95° C. for 5 minutes. The samples were then electrophoresized in SDS-PAGE gels (15% Tris-HCl ready gel made by Bio-Rad, Hercules, Calif.). After treatment with the fixing buffer (10% acetic acid, 10% methanol) and then the Amplify (Amersham-Pharmacia, Piscataway, N.J.), the gels were dried and exposed to X-ray film or quantitatively analyzed utilizing phosphor image (Molecular Dynamics, Sunnyview, Calif.).

A Vif-Vif binding assay was similar to the GST pull-down assays, except that the GST or GST-Vif conjugated bead slurry was mixed with $^{35}$S-labeled Vif and the test peptides or molecules in the binding buffer. The results were compared to that from the GST pull-down assay, which was designated as 100%.

In addition, in vitro translated, $^{35}$S-labeled Vif (50,000 cpm) was also directly loaded onto a 4-20% Tris-Glycine gel (SDS free) via 10% glycerol-containing loading buffer, with SDS at various concentrations, and electrophoresized with a SDS-free Tris-Glycine running buffer. After fixing and drying, the gel was directly subjected to autoradiography.

Western Blotting and Co-immunoprecipitation

The COS-1 or 293T cells were transfected with 5 µg pCI-vif-c-myc and pCI-vif-flag using calcium phosphate precipitation method. (Zhang, H., et al., *Proc. Natl. Acad. Sci. USA* 93(22):12519-24, 1996; Zhang, H., et al., *J. Virol.* 69(6):3929-32, 1995). After 48 hours, the cells were lyzed in a cell lysing buffer [150 mM NaCl, 50 mM Tris-HCl (pH8.0), 5 mM EDTA, 1% Triton-X-100, 10% glycerol, 1 mM PMSF, 2 µg/ml aprotinin, 2 µg/ml leupeptin, and 2 µg/ml pepstatin A]. For direct Western blotting, the whole cell lysates were mixed with acetone (1:3). The mixture was incubated on ice for 20 minutes, followed by centrifugation at 12,000 g for 10 minutes. The pellets were then air-dried and resuspended in SDS-containing sample buffer. The samples were electrophoresized in SDS-PAGE gels and then electronically transferred onto a nylon/nitrocellulose membrane. The primary antibodies, goat anti-c-Myc antibody (A14) (Research Antibodies, Santa Cruz, Calif.) or mouse anti-Flag antibody (M2) (Stratagene, La Jolla, Calif.) were used to bind the samples, respectively. The horseradish peroxidase (HPR)-conjugated anti-goat IgG antibody or anti-mouse IgG antibody (Research Antibodies, Santa Cruz, Calif.) were used as the secondary antibodies. A chemilufluminescence-based system (ESL, Amersham-Pharmacia Biotech, Piscataway, N.J.) was used to visualize the antigen-antibody binding.

For co-immunoprecipitation, cell lysates from COS-1 or 293T cells expressing Vif-Flag and/or Vif-c-Myc were incubated with A14 anti-c-Myc antibody (Research Antibodies, Santa Cruz, Calif.) (1 µg/ml) by mixing 12 hours at 4° C., followed by incubation with protein A-conjugated Sepharose CL-4B (Amersham-Pharmacia Biotech, Pis cataway, N.J.) for an additional 2 hours. The pellet was washed three times with cell lysing buffer and then resuspended in SDS-containing buffer, heated at 95° C., and centrifuged at 12,000 g. The supernatant was then subjected to SDS-PAGE. After transfer onto a nylon/nitrocellulose membrane, the samples were detected with a mouse M2 anti-Flag antibody. An HRP conjugated anti-mouse IgG-(Research Antibodies, Santa Cruz, Calif.) was used as a secondary antibody.

Mammalian Two-Hybrid System Assay

A mammalian two hybrid system, which was modified from the GAL4-based yeast two hybrid assay, was used to study the self-association of HIV-1 Vif proteins in vivo. (Shimano, R., et al., *Biochem. Biophys. Res. Comm.* 242(2):313-6, 1998; Bogerd, H., & Greene, W. C., *J. Virol.* 67(5):2496-502, 1993). The procedure was described, with some modifications, in Shimano, R., et al., *Biochem. Biophys. Res. Comm.* 242(2):313-6, 1998 and Bogerd, H., & Greene, W. C., *J. Virol.* 67(5):2496-502, 1993). Briefly, 5 µg pGal-Vif and pVif-VP were co-transfected with pG5BCAT into COS-1 cells using the Superfect transfection reagent (Qiagen, Valencia, Calif.). Forty-eight hours post-transfection, the cells were lyzed in reporter lysing buffer (Promega, Madison, Wis.) and subjected to a chloramphenicol acetyltransferase (CAT) assay, as described previously by Zhang, H., et al. in *J. Virol.* 69(6):3929-32, 1995.

Single-round viral infectivity assays

The biological activity of Vif mutants was evaluated by using a single-round viral infectivity assay as described in Dornadula, G., et al., *J. Virol.* 74(6):2594-602, 2000 with some modifications. To generate recombinant HIV-1 viruses, H9 cells were transfected with 5 µg pNL4-3ΔvifΔenv, pMD.G [containing VSV (vesicular stomatitis virus) envelope], and wild-type vif gene or its mutants (in pCI-neo construct) by electroporation. (Dornadula, G., et al., *J. Virol.* 74(6):2594-602, 2000; Naldini, L., et al., *Proc Natl Acad Sci USA* 93(21):11382-8, 1996). The electroporation (350 V, 250 µF, 5.1-6.3 msec) was performed by a gene pulser apparatus and capacitance (Bio-Rad, Hercules, Calif.). Thereafter, conditioned medium (RPMI 1640 plus 10% fetal bovine serum) was used to maintain the transfected H9 cells. Two days after transfection, the viral particles in supernatant were collected and pelleted via ultracentrifugation. (Dornadula, G., et al., *J. Virol.* 74(6):2594-602, 2000). After normalization by HIV-1 p24 antigen level, which was detected via enzyme-linked immunosorbent assays (ELISA, kits from DuPont), the viruses were used to infect $5 \times 10^5$ HeLa CD4-CAT cells. (Ciminale, V., et al., *AIDS Res. Hum. Retro.* 6(11):1281-7, 1990). Forty-eight hours post-infection, the cells were lyzed in reporter lysing buffer (Promega, Madison, Wis.) and subjected to CAT assays.

Phage Display Peptide Screening

Vif binding peptides displayed on M13 phages were screened using the Ph.D.-12™ Phage Display Peptide Library kit (New England Biolabs, Beverly, Mass.). Phage panning procedure was performed according to the kit protocol with some modifications. GST-Vif fusion protein attached on glutathione-agarose beads (Sigma, St. Louis, Mo.) was used as target for phage panning. For each round panning, $10^{11}$ phages were added to 10 mg GST attached on 3 ml glutathione-agarose gel in a final volume of 6 ml in TBS buffer (50 mM Tris-HCl, pH 7.5, 150 mM NaCl) and incubated for 1 hr at room temperature with shaking. The binding solution was separated by centrifugation at 500 g for 10 min and the supernatant was then added to 10 mg GST-Vif attached on 3 ml glutathione-agarose beads. The mixture was incubated for 1 hr at room temperature and then washed 6 times with TBST [50 mM Tris-HCl (pH 7.5), 500 mM NaCl, 0.5% Tween-20]. The GST-Vif binding phages were eluted by adding 3 ml of 5 mM reduced glutathione in TBS. The eluted phages were amplified by adding 2.5 ml of the elution to 20 ml of *E. coli* ER2738 culture (O.D at 0.6) and incubated at 37° C. with vigorous shaking for 4.5 hr. After centrifuge, the phages in the supernatant were precipitated by PEG/NaCl. After washing, the phages were suspended in 200 µl TBS. The titration of the eluted or amplified phages was determined as described in the kit protocol. After 3 round panning, individual phage plaques from the GST or GST-Vif elution tittering plates were selected for amplification respectively. Phage DNA was purified and sequenced.

Determination of Binding Affinity by ELISA

A phage enzyme-linked immunosorbent assay (ELISA) was performed to measure the relative binding affinity of phages to GST, GST-Vif, or GST-Vif without 151-192 amino acids. One hundred and fifty µl of 100 µg/ml GST and GST-Vif in 0.1 M NaHCO$_3$ (pH 8.6) were coated on 96 well microtiter plates respectively and incubated at 4° C. overnight. The plates were blocked with blocking buffer (0.1 M NaHCO$_3$, pH 8.6, 5 mg/ml BSA) for 2 hr at room temperature. The individual phage clones in 200 µl TBST were 4-fold-serially diluted (from $10^{11}$ to $10^5$) and added to the wells coated with GST, GST-Vif, or GST-Vif without 151-192 amino acids and incubated for 2 hr at room temperature. After washing, HRP-conjugated anti-M13 antibody was added to bind the phages. After washing, the substrate was added and color development was performed. The phages captured by Vif, therefore, were semi-quantitated. OD at 405 nm equal or larger than 0.15 was considered as positive.

Generation of Antibodies

The method of treating individuals exposed to or infected with HIV-1 in accordance with the present invention is based on the administration of compounds that interactively block, i.e., prevent or inhibit, the formation of Vif multimers, thereby inhibiting Vif function in the lentivirus life-cycle. According to the invention, Vif proteins, its fragments or other derivatives, or analogs thereof, may be used as an immunogen to generate antibodies that recognize such an immunogen. Such antibodies include, but are not limited to, single-chain, Fab fragments, and Fab expression library. In a specific embodiment, single-chain antibodies to a human protein are produced.

According to the invention, techniques described for the production of single chain antibodies (U.S. Pat. No. 4,946,778) can be adapted to produce Vif-specific single chain antibodies. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding (Bedzyk et al., 1990; Chaudhary et al., 1990). The linker is chosen to permit the heavy chain and light chain to bind together in their proper conformational orientation. See, for example, Huston, J. S., et al., *Methods in Enzym.* 203:46-121 (1991), which is incorporated herein by reference. These Fvs lack the constant regions (Fc) present in the heavy and light chains of the native antibody.

An additional embodiment of the invention utilizes the techniques described for the construction of Fab expression libraries (Huse, et al., *Science* 246:1275-1281, 1989) to allow rapid and easy identification of monoclonal Fab fragments with the desired specificity for Vif proteins, derivatives, or analogs.

Antibody fragments that contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; and the Fab fragments which can be generated by treating the antibody molecule with papain and a reducing agent.

In the production of antibodies, screening for the desired antibody can be accomplished by techniques known in the art.

Intracellular Expression Systems

Single-chain antibodies can be synthesized by a cell, targeted to particular cellular compartment, and used to interfere in a highly specific manner with HIV-1 replication. In the present invention, this method comprises the intracellular expression of a single-chain antibody that is capable of binding to a Vif protein, or derivative thereof, wherein the antibody preferably does not contain sequences coding for its secretion. Such single-chain antibodies will bind the target intracellularly. The antibodies of the present invention are expressed from a DNA sequence(s) that contains a sufficient number of nucleotides coding for the portion of an antibody capable of binding to the target. Due to the inherent degeneracy of the genetic code, other DNA sequences that encode substantially the same or a functionally equivalent heavy and light chain amino acid sequences, are within the scope of the invention. Altered DNA sequences that may be used in accordance with the invention include deletions, additions or substitutions of different nucleotide residues resulting in a sequence that encodes the same, or a functionally equivalent, gene product. The gene product itself may contain deletions, additions or substitutions of amino acid residues within a heavy or light chain sequence that result in a silent change, thus producing a functionally equivalent monoclonal antibody.

Single-chain antibody genes can be prepared using techniques known in the art. See U.S. Pat. No. 6,072,036, which is incorporated herein by reference. Preferably, the gene does not encode the normal leader sequence for the variable chains. The nucleotides coding for the binding portion of the antibody preferably do not encode the antibody's secretory sequences (i.e., the sequences that cause the antibody to be secreted from the cell). This type of design to leave out such sequences can readily be accomplished in the selection and omission of nucleotides coding for the antibody.

In addition, the gene is operably linked to a promoter or promoters that will permit expression of the antibody in the cell(s) of interest. Promoters that will permit expression in mammalian cells are well known in the art and can readily be selected depending on the target cell. Promoters include, but are not limited to, CMV, a viral LTR such as the rous sarcoma virus LTR, HIV-LTR, HTLV-1 LTR, the SV40 early promoter, *E. coli* lac UV5 promoter and the herpes simplex tk virus promoter. Furthermore, the use of inducible promoters, which are also well known in the art, in some embodiments are preferred. Then by "turning the promoter on" one can selectively obtain the expression of the antibody. The entire sequence(s) encoding the heavy and light chains of the single-chain antibody and promoter is described herein as an antibody cassette. The cassette is delivered to the cell by any of a number of means described below, which permit intracellular delivery of a gene. The cassette results in the intracellular expression of the antibody. The expressed antibody can then bind to the target antigen.

The antibodies of the present invention bind specifically to the target, i.e., the Vif protein, or derivative thereof, and can thus effectively inhibit Vif multimerization. To insure that the antibodies of the present invention can compete successfully with other molecules, they must retain at least about 75% of the binding effectiveness of the complete antibody to that target. More preferably, it has at least 85% of the binding effectiveness of the complete antibody. Still more preferably, it has at least 90% of the binding effectiveness of the complete antibody. Even more preferably, it has at least 95% of the binding effectiveness.

Gene Therapy

The antibody cassette is delivered to the cell by any of the known means. See for example, Miller, A. D., *Nature* 357: 455-460 (1992); Anderson, W. F., *Science* 256:808-813 (1992); Wu, et al, *J. of Biol. Chem.* 263:14621-14624 (1988). For example, a cassette containing these antibody genes, such as the sFv gene, can be targeted to a particular cell by a number of known forms of gene therapy according to the present invention. For general reviews of the methods of gene therapy, see Goldspiel et al., *Clinical Pharmacy* 12:488-505, 1993; Wu and Wu, *Biotherapy* 3:87-95, 1991; Tolstoshev, *Ann. Rev. Pharmacol. Toxicol.* 32:573-596, 1993; Mulligan, *Science* 260:926-932, 1993; and Morgan and Anderson, *Ann. Rev. Biochem.* 62:191-217, 1993; May, 1993, *TIBTECH* 11(5):155-215. Methods commonly known in the art of recombinant DNA technology that can be used are described in Ausubel et al. (eds.), 1993, *Current Protocols in Molecular Biology*, John Wiley & Sons, NY; and Kriegler, 1990, *Gene Transfer and Expression, A Laboratory Manual*, Stockton Press, NY.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286) (see infra), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide that is known to enter the nucleus, by administering it in linkage to a ligand subject to receptor-mediated endocytosis (see e.g., Wu and Wu, *J. Biol. Chem.* 262:4429-4432, 1987) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression by homologous recombination. (Koller & Smithies, *Proc. Natl. Acad. Sci. USA* 86:8932-8935, 1989; Zijlstra et al., *Nature* 342:435-438, 1989).

In a preferred aspect, the therapeutic agent comprises a nucleic acid encoding a Vif single-chain antibody, or functional derivative thereof, that is part of an expression vector that expresses a Vif antibody, or fragment thereof, in a suitable host. In particular, such a nucleic acid has a promoter operably linked to the Vif antibody coding region, the promoter being inducible or constitutive, and, optionally, tissue-specific. In another particular embodiment, a nucleic acid molecule is used in which the Vif antibody coding sequences and any other desired sequences are flanked by regions that promote homologous recombination at a desired site in the genome, thus providing for intrachromosomal expression of the Vif antibody nucleic acid. (Koller and Smithies, *Proc. Natl. Acad. Sci. USA* 86:8932-8935, 1989; Zijlstra et al., *Nature* 342:435-438, 1989).

Delivery of the nucleic acid into a patient is direct, i.e., the patient is directly exposed to the nucleic acid or nucleic acid-carrying vector. This approach is known, as in vivo gene therapy.

Proteins, Derivatives and Analogs Thereof

The invention further relates to Vif proteins, and derivatives (including but not limited to fragments) and analogs thereof, which bind to the multimerization domain of Vif protein thereby inhibiting Vif-Vif interaction and Vif protein multimerization. Molecules comprising Vif proteins or derivatives also are provided.

The production and use of derivatives and analogs related to Vif are within the scope of the present invention. In a specific embodiment, the derivative or analog is an antagonist capable of interactively binding Vif but incapable of exhibiting the functional activities associated with a full-length, wild-type protein. Such derivatives or analogs that have the desired immunogenicity or antigenicity can be used, for example, for inhibition of Vif activity. Derivatives or analogs that lack or inhibit a desired Vif property of interest (e.g., inhibition of infectivity) can be used as inhibitors of such property and its physiological correlates. A specific embodiment relates to a Vif fragment that can be bound or otherwise associated with Vif itself, thereby preventing or interfering with Vif multimerization. Derivatives or analogs of Vif can be tested for the desired activity by procedures known in the art.

In a specific embodiment of the invention, proteins consisting of, or comprising a fragment of, a Vif protein consisting of at least the amino acid sequence substantially corresponding to the amino acid sequence from amino acid residue 144-177 (SEQ. ID. NO: 26), preferably, 151-164 (SEQ. ID. NO: 1), and more preferably, 161-164 (SEQ. ID. NO: 25), are provided. Derivatives or analogs of Vif having amino acid residues 144-171, preferably, 151-164, more preferably, 161-164, or a sequence substantially corresponding thereto, include but are not limited to those molecules comprising regions that are substantially homologous to Vif or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding vif sequence, under stringent, moderately stringent, or nonstringent conditions.

"Stringent conditions" as used herein refers to those hybridizing conditions that (Virgilio, L., et al., 1994, Proc Natl Acad Sci USA, 91:12530-12534) employ low ionic strength and high temperature for washing, for example, 0.015 M NaCl/0.0015 M sodium citrate/0.1% SDS at 50° C.; (Narducci, M. G., et al., 1997, Cancer Res, 57:5452-5456) employ, during hybridization, a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (Virgilio, L., et al., 1998, Proc Natl Acad Sci USA, 95:3885-3889) employ 50% formamide, 5×SSC (0.75 M NaCl, 0.075 M sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

"Moderately stringent conditions" or "nonstringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of "moderately stringent conditions" is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 µg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. An example of "nonstringent conditions" is overnight incubation at 37° C. in a solution comprising: 5×SSC, 25% formamide, 5×Denhardts solution, 10% dextran sulfate, and 100 g/ml denatured salmon sperm DNA followed by washing the filters in 5×SSC, 0.1% SDS at room temperature.

The Vif derivatives and analogs of the invention can be produced by various methods known in the art. The manipulations that result in their production can occur at the gene or protein level. Still within the scope of the present invention, other sterically similar compounds, called peptidomimetics, may be formulated to mimic the key portions of the structure of Vif protein, derivatives and analogs thereof. Such compounds may be used in the same manner as Vif protein, derivatives and analogs thereof and hence are also functional equivalents. The generation of a structural functional equivalent may be achieved by the techniques of modeling and chemical design known to those of skill in the art. It will be understood that all such sterically similar constructs fall within the scope of the present invention.

Additionally, the vif encoding nucleic acid sequence can be mutated in vitro or in vivo to create and/or destroy translation, initiation, and/or termination sequences, or to create variations in coding regions and/or form new restriction endonuclease sites or destroy preexisting ones to facilitate further in vitro modification. Any technique for mutagenesis known in the art can be used, including but not limited to, chemical mutagenesis, in vitro site-directed mutagenesis (Hutchinson, C., et al., *J. Biol. Chem.* 253:6551, 1978), etc.

Manipulations of the Vif sequence also may be made at the protein level. Included within the scope of the invention are protein fragments or other derivatives or analogs that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Vif can be chemically synthesized. For example, a peptide corresponding to a portion of a Vif protein that comprises the desired domain, or which mediates the desired activity in vitro, can be synthesized by use of a peptide synthesizer. Furthermore, if desired, nonclassical amino acids or chemical amino acid analogs can be introduced as a substitution or addition into the Vif sequence. Non-classical amino acids include but are not limited to the D-isomers of the common amino acids, α-amino isobutyric acid, 4amino-butyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, C-α-methyl amino acids, N-α-methyl amino acids, and amino acid analogs in general. Furthermore, the amino acid can be D (dextrorotary) or L (levorotary).

In a specific embodiment, the Vif derivative is a chimeric, or fusion, protein comprising a Vif protein or fragment thereof (consisting of at least the sequence from amino acid residue 144-171, preferably, 151-164, more preferably, 161-164) joined at its amino- or carboxy-terminus via a peptide bond to an amino acid sequence of a different protein. In one embodiment, such a chimeric protein is produced by recombinant expression of a nucleic acid encoding the protein (comprising a Vif-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of vif fused to any heterologous protein-encoding sequences may be constructed.

In another specific embodiment, the Vif derivative is a molecule comprising a region of homology with a Vif protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a Vif domain or a portion thereof or a full-length protein.

Also provided by the present invention are molecules comprising one or more peptidomimetics of a Vif domain or a portion thereof or a full-length protein.

PXP Motif-Containing Peptides

The present invention also relates to peptides containing PXP motifs. Molecules comprising PXP motif-containing peptides also are provided.

The PXP motif-containing peptides may be about 5 to 20 amino acids long. By way of example, but not by way of limitation, such PXP motif-containing peptides may include peptides with amino acid sequence of SEQ. ID. NO: 5-23.

The production and use of PXP motif-containing peptides are within the scope of the present invention. In a specific embodiment, the PXP motif-containing peptides are antagonists capable of interactively binding to the multimerization domain of Vif protein and inhibiting Vif protein multimerization. Still within the scope of the present invention, other sterically similar compounds, called peptidomimetics, may be formulated to mimic the key portions of the structure of PXP motif-containing peptide. Such compounds may be used in the same manner as the PXP motif-containing peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

The PXP motif-containing peptides of the invention can be produced by various methods known in the art. For example, PXP motif-containing peptides can be chemically synthesized by use of a peptide synthesizer. Furthermore, if desired, nonclassical amino acids or chemical amino acid analogs can be introduced as a substitution or addition into the PXP motif-containing peptides. Non-classical amino acids include but are not limited to the D-isomers of the common amino acids, α-amino isobutyric acid, 4 amino-butyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, C-α-methyl amino acids, N-α-methyl amino acids, and amino acid analogs in general. Furthermore, the amino acid can be D (dextrorotary) or L (levorotary).

In a specific embodiment, a PXP motif-containing peptide is a chimeric, or fusion, protein comprising a PXP motif-containing peptide joined at its amino- or carboxy-terminus via a peptide bond to an amino acid sequence of a different protein. In one embodiment, such a chimeric protein is produced by recombinant expression of a nucleic acid encoding the protein (comprising a coding sequence for the PXP motif-containing peptide joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising coding sequence for PXP motif-containing peptides fused to any heterologous protein-encoding sequences may be constructed.

In other specific embodiment of the invention, molecules comprising PXP motif-containing peptides are provided. A molecule can comprise one or more PXP motif-containing peptides. A PXP motif-containing peptides may be 5 to 20 amino acids long. By way of example, but not by way of limitation, such PXP motif-containing peptides may include peptides with amino acid sequences of SEQ. ID. NO: 5-23.

Also provided are molecules comprising one or more peptidomimetics of PXP motif-containing peptides. Such PXP motif-containing peptides include, but are not limited to, peptides with amino acid sequences of SEQ. ID. NO: 5-23.

Screening for Small Molecules Inhibiting Vif Multimerization

The present invention relates to the detection of molecules that specifically bind to Vif, thereby inhibiting its multimerization. Such molecules will thus inhibit the HIV-1 life-cycle. In a preferred embodiment, assays are performed to screen for molecules with potential utility as therapeutic agents or lead compounds for drug development. The invention provides assays to detect molecules that bind to Vif and antagonize Vif multimerization, thereby inhibiting the activity of Vif and subsequent replication of the lentivirus.

For example, recombinant cells expressing Vif nucleic acids are used to recombinantly produce Vif or Vif conjugate and screen for molecules that bind to Vif or Vif conjugate. Molecules are contacted with the Vif or Vif conjugate, or fragment thereof, under conditions conducive to binding, and then molecules that specifically bind to the Vif or Vif conjugate are identified. Methods that are used to carry out the foregoing are commonly known in the art. By way of example, but not way of limitation, phage peptide display assay or phage enzyme-linked immunosorbent assay (ELISA) may be used.

In another embodiment of the present invention, molecules that bind to Vif or Vif conjugate and inhibit Vif protein multimerization may be identified by Vif-Vif binding assay. More specifically, Vif-Vif binding assay comprises the steps of, 1) conjugating Vif or Vif-containing peptides to a column or beads; 2) applying a test molecule and labeled Vif, or fragments thereof, that contains the multimerization domain on the Vif- or Vif-containing peptide-conjugated column or beads; 3) washing the column or beads and dissociating the labeled Vif, or fragments thereof, from the column or beads; and 4) measuring and comparing the amount of labeled Vif, or fragments thereof, that was bound to the column or beads to determine the antagonism activity of the molecule. By "labeled Vif or fragments thereof," it is referred to, but not limited to, radio labeled, chemical labeled, or fluorescent labeled.

In a specific embodiment of the present invention, Vif and/or cell line that expresses Vif is used to screen for antibodies, peptides, or other molecules that bind to Vif and act as an antagonist of Vif. The antagonists of the present invention will function in any cell. The Vif antagonists of the present invention will bind to the multimerization domain of Vif, preventing Vif self-association, thereby inhibiting or preventing the replicative and other essential functions of Vif. Therefore, Vif antagonists will inhibit or prevent a disease state or condition associated with lentivirus infection. Such disease states include, but are not limited to, acquired immunodeficiency syndrome.

Vif antagonists are identified by screening organic or peptide libraries with recombinantly expressed Vif. These Vif antagonists are useful as therapeutic molecules, or lead compounds for the development of therapeutic molecules, to modify the activity of Vif. Synthetic and naturally occurring products are screened in a number of ways deemed routine to those of skill in the art.

By way of example, diversity libraries, such as random or combinatorial peptide or nonpeptide libraries are screened for molecules that specifically bind to Vif. Many libraries are known in the art that are used, e.g., chemically synthesized libraries, recombinant (e.g., phage display libraries), and in vitro translation-based libraries.

Examples of chemically synthesized libraries are described in (Fodor, et al., *Science* 251:767-773, 1991; Houghten, et al., *Nature* 354:84-86, 1991; Lam, et al., *Nature* 354:82-84, 1991; Medynski, *Bio/Technology* 12:709-710, 1994; Gallop, et al., *J. Medicinal Chemistry* 37(9):1233-1251, 1994; Ohlmeyer, et al., *Proc. Natl. Acad. Sci. USA* 90:10922-10926, 1993; Erb, et al., *Proc. Natl. Acad. Sci. USA* 91:11422-11426, 1994; Houghten, et al., *Biotechniques* 13:412, 1992; Jayawickreme, et al., *Proc. Natl. Acad. Sci. USA* 91:1614-1618, 1994; Salmon, et al., *Proc. Natl. Acad. Sci. USA* 90:11708-11712, 1993; PCT Publication No. WO 93/20242; and Brenner & Lerner, *Proc. Natl. Acad. Sci. USA* 89:5381-5383, 1992).

Examples of phage display libraries are described in (Scott & Smith, *Science* 249:386-390, 1990; Devlin, et al., *Science*, 249:404-406, 1990; Christian, R. B., et al., *J. Mol. Biol.* 227:711-718, 1992; Lenstra, *J. Immunol. Meth.* 152:149-157, 1992; Kay, et al., *Gene* 128:59-65, 1993; PCT Publication No. WO 94/18318 dated Aug. 18, 1994).

In vitro translation-based libraries include, but are not limited to, those described in PCT Publication No. WO 91/0505 dated Apr. 18, 1991; Mattheakis, et al., *Proc. Natl. Acad. Sci. USA* 91:9022-9026, 1994.

By way of examples of nonpeptide libraries, a benzodiazepine library (see e.g., Bunin, et al., *Proc. Natl. Acad. Sci. USA* 91:4708-4712, 1994) can be adapted for use. Peptoid libraries (Simon, et al., *Proc. Natl. Acad. Sci. USA* 89:9367-9371, 1992) also can be used. Another example of a library that can be used, in which the amide functionalities in peptides have been permethylated to generate a chemically transformed combinatorial library, is described by Ostresh, et al. in *Proc. Natl. Acad. Sci. USA* 91:11138-11142, 1994.

Screening the libraries is accomplished by any of a variety of commonly known methods. See, e.g., the following references, which disclose screening of peptide libraries: Parmley & Smith, *Adv. Exp. Med. Biol.* 251:215-218, 1989; Scott & Smith, *Science* 249:386-390, 1990; Fowlkes, et al., *BioTechniques* 13:422-427, 1992; Oldenburg, et al., *Proc. Natl. Acad. Sci. USA* 89:5393-5397, 1992; Yu, et al., *Cell* 76:933-945, 1994; Staudt, et al., *Science* 241:577-580, 1988; Bock, et al., *Nature* 355:564-566, 1992; Tuerk, et al., *Proc. Natl. Acad. Sci. USA* 89:6988-6992, 1992; Ellington, et al., *Nature* 355: 850-852, 1992; U.S. Pat. No. 5,096,815, U.S. Pat. No. 5,223, 409, and U.S. Pat. No. 5,198,346, all to Ladner, et al.; Rebar & Pabo, Science 263:671-673, 1993; and PCT Publication No. WO 94/18318.

In a specific embodiment, screening is carried out by contacting the library members with Vif, or fragment thereof, immobilized on a solid phase and harvesting those library members that bind to the Vif, or fragment thereof. Examples of such screening methods, termed "panning" techniques, are described by way of example in Parmley & Smith, *Gene* 73:305-318, 1988; Fowlkes, et al., *BioTechniques* 13:422-427, 1992; PCT Publication No. WO 94/18318 and in references cited hereinabove.

In another embodiment, the two-hybrid system for selecting interacting proteins in yeast (Fields & Song, *Nature* 340: 245-246, 1989; Chien et al., *Proc. Natl. Acad. Sci. USA* 88:9578-9582, 1991) is used to identify molecules that specifically bind to Vif, or fragment thereof.

Therapeutic uses

The invention provides for treatment or prevention of various diseases, disorders, and conditions by administration of a therapeutic compound. Such therapeutics include but are not limited to Vif proteins and analogs and derivatives (including fragments) thereof; antibodies thereto; nucleic acids encoding the proteins, analogs, or derivatives; and antagonists. In a preferred embodiment, disorders involving lentivirus infection are treated or prevented by administration of a therapeutic that inhibits Vif function.

Generally, administration of products of a species origin or species reactivity (in the case of antibodies) that is the same species as that of the patient is preferred. Thus, in a preferred embodiment, a human Vif protein, derivative, or analog, or nucleic acid, or an antibody to a human Vif protein or human Vif nucleic acid, is therapeutically or prophylactically administered to a human patient.

A vif polynucleotide and its protein product can be used for therapeutic/prophylactic purposes for diseases and conditions involving lentivirus infection, as well as other disorders associated with the multimerization of Vif. A vif polynucleotide, and its protein product, may be used for therapeutic/prophylactic purposes alone or in combination with other therapeutics useful in the treatment of acquired immunodeficiency syndrome or other diseases and conditions caused by lentiviruses.

In specific embodiments, therapeutics that inhibit Vif function are administered therapeutically (including prophylactically): (1) in diseases, disorders, or conditions involving lentiviruses, specifically HIV-1; or (2) in diseases, disorders, or conditions wherein in vitro (or in vivo) assays indicate the utility of Vif antagonist administration. The presence of HIV-1 can be readily detected by any means standard in the art, e.g., by obtaining a patient blood sample and assaying it in vitro for the presence of HIV-1.

Therapeutic/prophylactic methods

The invention provides methods of treatment and prophylaxis by administration to a subject of an effective amount of a therapeutic, i.e., a monoclonal (or polyclonal) antibody, retroviral vector, or Vif antagonist of the present invention. In a preferred aspect, the therapeutic is substantially purified. The subject is preferably an animal, including but not limited to, animals such as cows, pigs, chickens, etc., and is preferably a mammal, and most preferably human.

Various delivery systems are known and are used to administer a therapeutic of the invention, e.g., encapsulation in liposomes, microparticles, microcapsules, expression by recombinant cells, receptor-mediated endocytosis (see, e.g., Wu & Wu, *J. Biol. Chem.* 262:4429-4432, 1987), construction of a therapeutic nucleic acid as part of a retroviral or other vector, etc. Methods of introduction include, but are not limited to, intradermal, intramuscular, intraperitoneal, intravenous, subcutaneous, intranasal, and oral routes. The compounds are administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. In one embodiment, administration is by direct injection at the site (or former site) of a malignant tumor or neoplastic or pre-neoplastic tissue.

In a specific embodiment where the therapeutic is a nucleic acid encoding a protein therapeutic the nucleic acid is administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot, et al., *Proc. Natl. Acad. Sci. U.S.A.* 88:1864-1868, 1991), etc. (supra). Alternatively, a nucleic acid therapeutic can be introduced intracellularly and incorporated within host cell DNA for expression by homologous recombination (supra).

Pharmaceutical compositions

The present invention also provides pharmaceutical compositions. Such compositions comprise a therapeutically effective amount of a therapeutic and a pharmaceutically acceptable carrier or excipient. Such a carrier includes, but is not limited to, saline, buffered saline, dextrose, water, glycerol, ethanol, and combinations thereof. The carrier and composition can be sterile. The formulation will suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

The therapeutics of the invention are formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention that will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation also will depend on the route of administration, and the seriousness of the disease, disorder, or condition and is decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10 k by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Results

Vif Proteins can Form Multimers In Vitro

To examine whether Vif proteins have a tendency towards self-association, GST-Vif was expressed in BL 21 bacterial cells and isolated onto glutathione-conjugated agarose beads. The GST-Vif-conjugated beads were then incubated with in vitro translated, $^{35}$S-labeled Vif proteins. After binding, the bead-associated $^{35}$S-labled Vif was analyzed by SDS-PAGE, followed by direct autoradiography. The autoradiograph of the bound $^{35}$S-labled Vif illustrates that GST-Vif (lane 2), but not GST (lane 3), binds to $^{35}$S-labeled, in vitro translated Vif protein, indicating a Vif-Vif interaction (FIG. 1A).

Figure 1B:
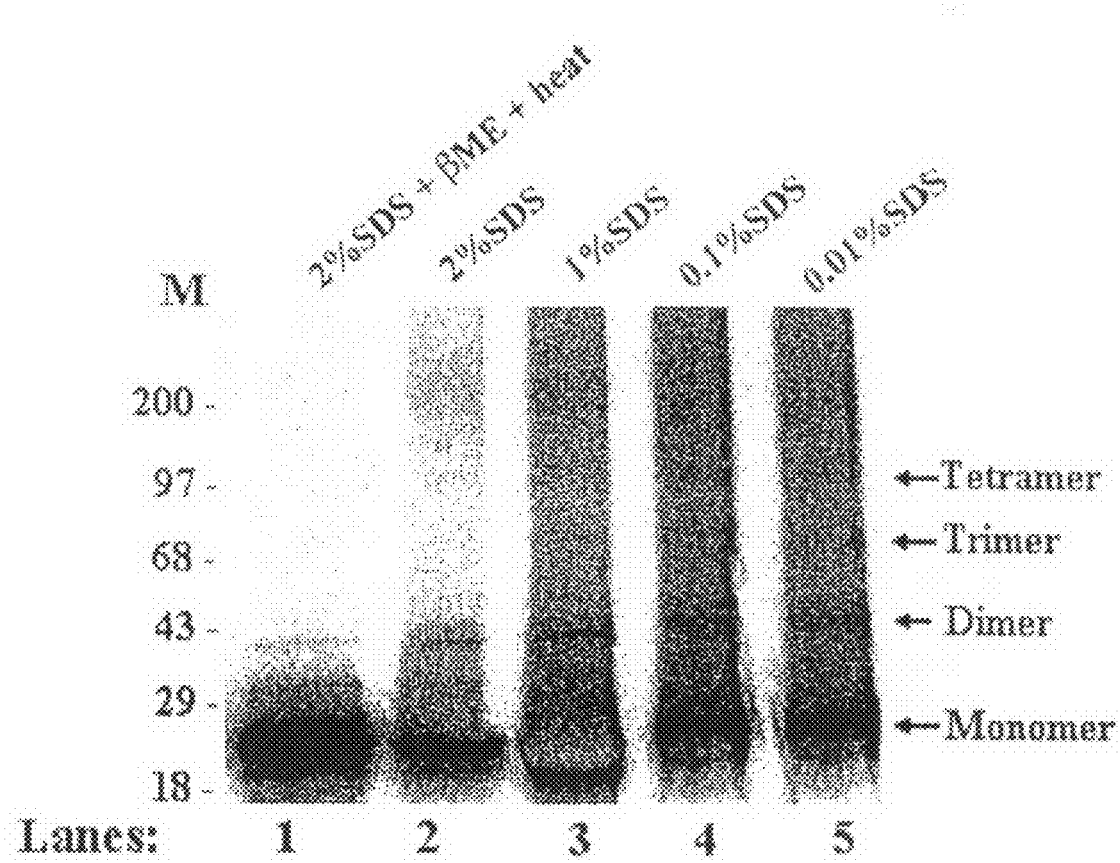

To further evaluate the tendency of Vif proteins to self-associate, in vitro translated, $^{35}$-labeled HIV-1 Vif proteins were directly loaded onto a Tris-Glycine-native gel (SDS-free) with loading buffers containing 10% glycerol only or SDS at various concentrations. Electrophoresis performed with a 4-15% Tris-Glycine running buffer shows that, at the native or relatively native conditions, the $^{35}$S-labeled Vif proteins migrate as monomers (23 Kd), dimers (46 Kd), trimers (69 Kd), or tetramers (92 Kd) (FIG. 1B). With the increment of concentrations of SDS in the loading buffer, the major form of Vif eventually becomes a monomer (23 Kd). When the sample was heated at 95° C. for 5 minutes, all the multimers of Vif proteins disappeared, implying that the Vif-Vif binding is not covalent. Since, prior to the sample loading, $^{35}$S-labeled, in vitro translated HIV-1 Vif protein was treated with RNase A to remove possible RNA contamination, the Vif-Vif binding was RNA-independent.

The Binding Site for Vif Multimerization is Located in the C-terminus

Figure 2A:
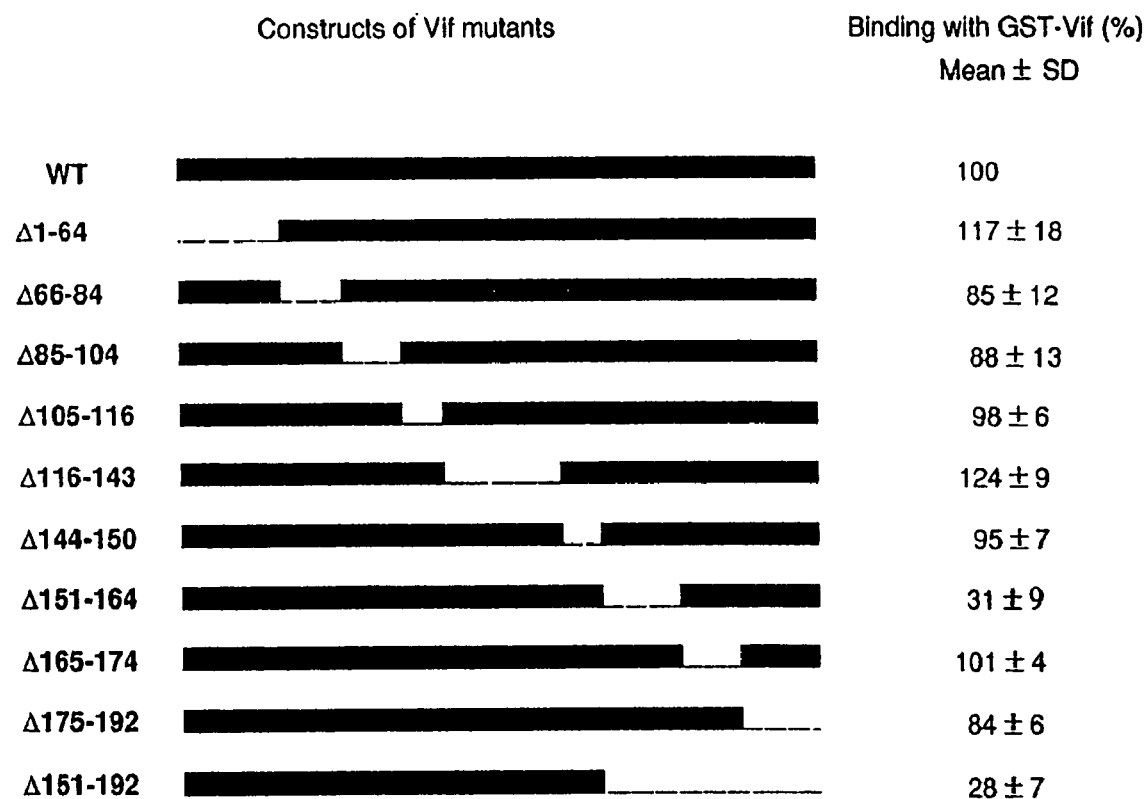
Figure 2B:
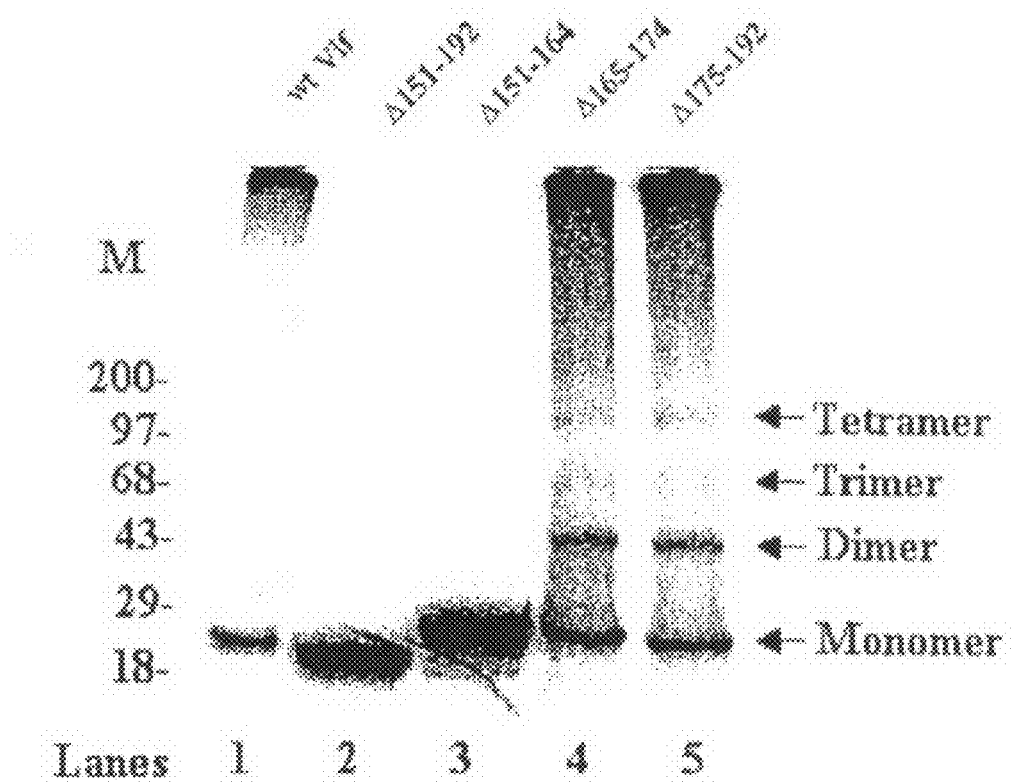

To determine the binding sites for Vif multimerization, a series of deletions in Vif protein are generated through PCR-based mutagenesis, followed by in vitro translation in the presence of $^{35}$S-methionine. These Vif mutants were then allowed to bind to GST-Vif fusion protein conjugated on agarose beads. After binding, the bead-associated, $^{35}$S-labeled Vif protein and its mutants were subjected to SDS-PAGE and visualized by direct autoradiography. FIG. 2A presents the results. Vif protein severely loses the Vif-Vif binding activity with deletion of the C-terminus, while deletion at amino acid positions 151-164 significantly decreases the binding ability (FIG. 2A). This result is confirmed by native multimer formation assay. In the presence of 0.1% SDS, Vif mutants A151-192 and A151-164 were unable to form multimers, while other mutants retained the ability to multimerize (FIG. 2B).

It is notable that there are several positively-charged amino acids in the 151-164 fragment. The mutants that substitute these positively-charged amino acids as generated by Goncalves et al. (Goncalves, J., et al., *J. Virol.* 69(11):7196-204, 1995) have been examined for this Vif-Vif binding. However, all these mutants still contain Vif-Vif binding ability (data not shown). It is also notable that there are several prolines (P156, P161, P162, P164) in this fragment. Among these prolines, P161 is highly conserved in various strains of HIV-1 or SIV. Further investigation demonstrates that deletion of $^{161}$PPLP$^{164}$ (aa 161-164 in Vif protein, SEQ. ID. NO: 25) significantly impairs the capability of Vif proteins to interact each others. Moreover, a highly conerved motif, SLQYLAL (SEQ. ID. NO: 4) (amino acid positions 144-150 for HIV-$1_{NL4-3}$), is close to this domain.

The domain for Vif multimerization, therefore, is located at the C terminus, more particularly, amino acid positions 144-171 of HIV$_{NL4-3}$ Vif protein and has the amino acid sequence of SEQ. ID. NO: 26.

Vif to Vif Interactions within a Cell

To examine whether Vif self-association also occurs intracellularly, a co-immunoprecipitation method was utilized. The Vif protein was tagged with either c-Myc (SEQ. I.D. NO: 3) or Flag epitope (SEQ. I.D. NO: 2) at its C-terminus and expressed in COS-1 cells. The expression of c-Myc-tagged Vif and Flag-tagged Vif was detected via Western blotting with mouse anti-c-Myc epitope antibody or goat anti-Flag epitope antibody, respectively (FIG. 3, top two panels). To study Vif-Vif interaction, the cell lysates were immunoprecipitated with anti-Myc antibody and then subjected to SDS-PAGE, followed by Western blotting. The goat anti-Flag antibody was used to detect Flag-tagged Vif. The results are shown in FIG. 3, bottom panel. The Flag-tagged Vif is co-precipitated with Myc-tagged Vif when mouse anti-Myc antibody was utilized for the immunoprecipitation, implying a Vif-Vif interaction within a cell (FIG. 3, bottom panel).

Figure 4A:
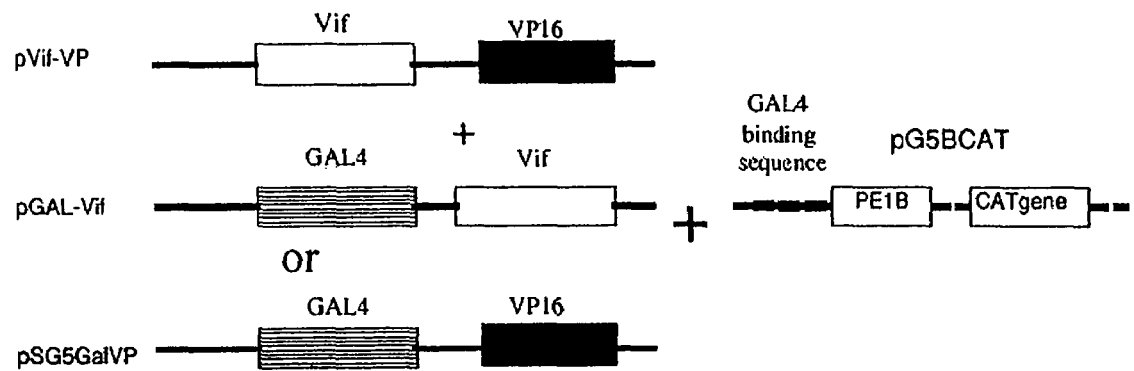
Figure 4B:
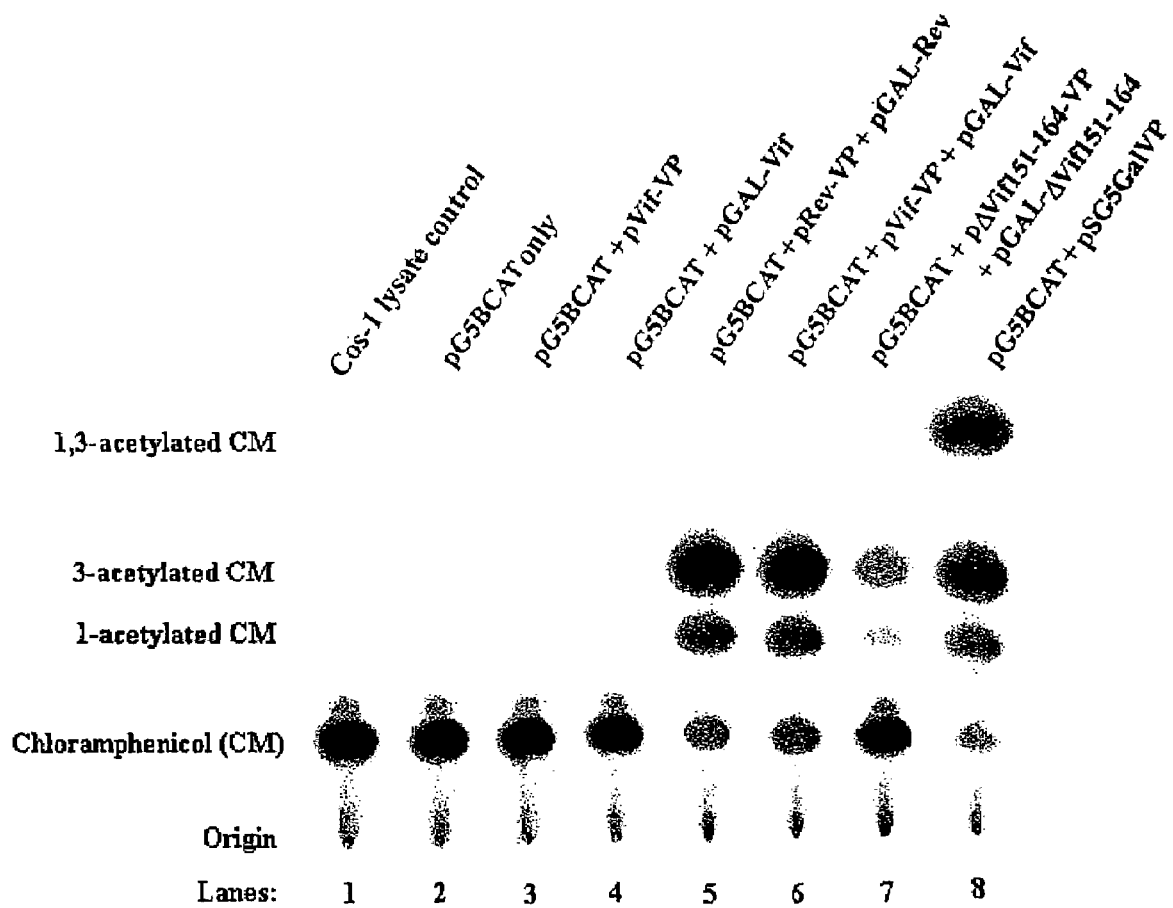

Alternatively, the in vivo Vif to Vif interaction was examined by the mammalian two-hybrid system. A fusion protein composed of VP16 and Gal4 is able to activate Gal4-response element-contained E1b promoter. Gal4 functions as a DNA-binding domain, while VP16 functions as a DNA activation domain. HIV-1 Vif protein is allowed to replace the VP16 or Gal4 domain, respectively (FIG. 4A). If the interaction between Vif proteins takes place, the VP16 and Gal4 domains are brought together and the Gal4-binding-sequence-contained in the E1b promoter is activated. CAT analysis revealed that, like Rev-Rev interactions, Vif in Vif-VP16 fusion protein binds to Vif in the Gal4-Vif fusion protein and activates the expression of CAT (lane 6) (FIG. 4B). As controls, pGal-Vif or pVif-VP alone were unable to activate CAT expression (lanes 3 & 4, FIG. 4B). FIG. 4B also shows that Vif mutant Δ151-164, which does not have the ability to interact with Vif protein in other systems, does not interact with Vif in this system (lane 7).

Deletion of the Vif-Vif Binding Domain Severely Decreases the Vif Function in the Viral Life Cycle.

As mentioned previously, Vif functions in the late stages of the HIV-1 life-cycle and is required by "non-permissive" cells, such as PBMC, macrophages, and H9 T-cells, for HIV-1 replication. (Gabuzda, D. H., et al., *J. Virol.* 66(11):6489-95, 1992; Blanc, D., et al., *Virology* 193(1):186-92, 1993; von Schwedler, U., et al., *J. Virol.* 67(8):4945-55, 1993). To investigate the physiological significance of Vif multimerization, the ability of Vif mutant Δ151-164 to complement Vif function in the viral life-cycle was examined. Vif mutant Δ151-164 was used because it is unable to form multimers in cell-free systems and within cells. To this end, a single-round viral infectivity assay was adapted. Wild-type Vif or its mutants, were expressed in the "non-permissive" H9 T-cells. At the same time, pseudotyped (with VSV envelope) HIV-1 viruses, without vif and env in their genome, were generated from these cells. After ultracentrifugation for enrichment, the recombinant viruses were allowed to infect the target cells (Hela CD4-CAT), which harbor an expression cassette containing HIV-1 LTR promoter-driven CAT gene. The viral infectivity was measured by the level of CAT gene expression in the target cells, which is driven by the HIV-1 Tat protein expressed by the newly-synthesized proviruses. FIG. 5 demonstrates that, when the wild-type vif gene is expressed in the vif-defective HIV-1 virus-producing "non-permissive" H9 T-cells, the viral infectivity reaches a high level (lane 2). When Vif Δ151-164 is expressed in the vif-defective HIV-1 virus-producing "non-permissive" H9 T-cells, however, the viral infectivity is unaltered (lane 3) compared to the vif-defective HIV-1 viruses (lane 4) (FIG. 5). These data indicate that the 151-164 deletion severely decreases the function of Vif protein and makes it unable to rescue the infectivity of the vif-defective HIV-1 viruses generated from "non-permissive" T-cells. The results demonstrate that multimerization of Vif proteins is required for Vif function.

Peptides Containing PXP Motif Inhibit Vif-Vif Interaction by Binding to PPLP Domain To further identify peptides that bind to the Vif protein multimerization domain, thereby inhibiting Vif-Vif interaction and viral infectivity of HIV-1 virus, a set of 12-mer peptides containing a PXP motif (Table 1, SEQ. ID. NO: 5-20) was constructed, which structure is shared by the $^{161}$PPLP$^{164}$ domain (SEQ. ID. NO: 25) of Vif protein. Through phage peptide display method, it was demonstrated that these peptides bind to purified HIV-1 Vif protein at high affinity (FIG. 6). Some of these peptides were synthesized and were added into the reaction system for Vif-Vif binding. As shown in Table 1, peptides containing PXP motif such as LPLPAPSFHRTT (VMI9, SEQ. ID. NO: 13) or SNQGGSPLPRSV (VMI7, SEQ. ID. NO: 11) can significantly inhibit Vif-Vif interaction.

Further experiments demonstrated that PXP motif-containing peptides were unable to bind to $^{161}$PPLP$^{164}$ domain-deleted-VIF protein, thereby evidencing that the $^{161}$PPLP$^{164}$ domain plays a key role in Vif multimerization and that PXP motif-containing peptides block the multimerization of Vif through binding to the $^{161}$PPLP$^{164}$ domain of Vif protein.

A set of synthesized Vif peptides, Vif155-166 (SEQ. ID. NO: 21), Vif157-171 (SEQ. ID. NO: 23), Vif161-175 (SEQ. ID. NO: 22), and Vif117-131 (SEQ. ID. NO: 24) were screened for their ability to block the Vif-Vif interaction in vitro. As shown in Table 1, three peptides, Vif155-166 (SEQ. ID. NO: 21), Vif157-171 (SEQ. ID. NO: 23), and Vif161-175 (SEQ, ID. NO: 22), which contain the $^{161}$PPLP$^{164}$ domain, were able to inhibit the Vif-Vif interaction, further supporting that the $^{161}$PPLP$^{164}$ domain is responsible for Vif multimerization.

TABLE 1

Inhibitory Effect of Peptides containing PXP Motif upon Vif-Vif Interaction

| SEQ. ID. NO: | peptide | $^{35}$S-Vif binds with GST-Vif (%) Mean ± SD |
|---|---|---|
| | No peptide | 100 |
| 5 (VMI1) | SNFASITTPRPH | ND |
| 6 (VMI2) | WPTNPTTVPVPS | ND |
| 7 (VMI3) | LTSDTYFLPVPA | ND |
| 8 (VMI4) | SLHWPVSHPPPP | ND |
| 9 (VMI5) | SVSVGMKPSPRP | 36.3 + 5.1 |
| 10 (VMI6) | WHSQRLSPVPPA | ND |
| 11 (VMI7) | SNQGGSPLPRSV | 19.0 + 2.2 |
| 12 (VMI8) | SEPHLPFPVLPH | ND |
| 13 (VMI9) | LPLPAPSFHRTT | 22.0 + 6.2 |
| 14 (VMI10) | YPLPHPMWSMLP | ND |
| 15 (VMI11) | TMTPPPTSVRGT | ND |
| 16 (VMI12) | TPLPTIRGDTGT | ND |
| 17 (VMI13) | GPPPHHRDYHGP | ND |
| 18 (VMI14) | YPAPIKVLLPNS | ND |
| 19 (VMI15) | SPYPMALFPLHN | ND |
| 20 (VMI16) | SPYPSWSTPAGR | ND |
| 21 (Vif155-166) | KPKKIKPPLPSV | 57.1 + 8.7 |
| 22 (Vif161-175) | PPLPSVTKLTEDRWN | 70.2 + 5.5 |
| 23 (Vif157-171) | KKIKPPLPSVTKLTE | 49.2 + 2.5 |
| 24 (Vif117-131) | ESAIRKAILGHIVSP | 94.5 + 11.2 |

Discussion

The formation of dimers or multimers by many HIV-1 proteins, e.g., Gag, protease, reverse transcriptase, integrase, glycoprotein 41(gp41), Tat, Rev, Vpr, and Nef, has been shown to be important for their functions in the lentiviral life-cycle. (Frankel, A. D. & Young, J. A., *Ann. Rev. Biochem.* 67:1-25, 1998; Vaishnav, Y. N. & Wong-Staal, F., *Annu Rev Biochem* 60:577-630, 1991; Zhao, L. J., et al., *J Biol Chem* 269(51):32131-7, 1994; Liu, L., et al., *J. Virol.* 74.5310-5319, 2000). In addition, multimerization is critical to the biological activity of many prokaryotic and eukaryotic proteins and is a common mechanism for the functional activation/inactivation of proteins. The present invention demonstrates that HIV-1 Vif proteins form dimers or multimers and that such multimerization is essential for Vif function in the viral life-cycle. The evidence reveals that in vitro translated $^{35}$S-labeled Vif proteins are able to form multimers in the native environment. Conversely, GST-Vif fusion proteins, rather than GST proteins, which are generated from a bacterial expression system, are able to bind to the in vitro translated $^{35}$S-labeled Vif proteins. Further, results of co-immunoprecipitation and a mammalian two hybrid system demonstrate a Vif-Vif interaction intracellularly. These in vitro and in vivo data strongly imply that Vif proteins are able to form multimers. Deletion of the domain essential for Vif-Vif binding severely decreases the function of Vif in the "non-permissive" cells, evidencing further that multimerization of Vif is important for its function in the HIV-1 life-cycle.

The domain for Vif multimerization is located in a positively-charged amino acid- and proline-enriched fragment (amino acid positions 144-171) and has the amino acid sequence of SEQ. I.D. NO: 26. (FIG. 2). The positively-charged amino acids in this region are not responsible for the Vif-Vif interaction. However, the prolines, more particularly, the $^{161}$PPLP$^{164}$ domain is responsible for Vif multimerization (FIG. 6 and Table 1). Based on this, a set of PXP motif-containing peptides are identified as inhibitors of Vif protein multimerization. It is notable that a highly conserved motif, SLQYLAL (SEQ. I.D. NO: 4) (amino acid positions 144-150 for HIV-1$_{NL4-3}$), is close to this domain. It also has been shown that serine165 is phosphorylated by the mitogen-activated protein kinase (p44/42) of Vif and that this phosphorylation is important for Vif function. (Yang, X., & Gabuzda., D., *J. Bio. Chem.* 273(45):29879-87, 1998). As these residues are close to the domain for multimerization, it is possible that the multimerization of Vif proteins is regulated by phosphorylation in the virus-producing cells.

Interestingly, the positively-charged amino acids (replaced in B4 and B7 mutants) in the C-terminus of Vif are responsible for Vif-NCp7 binding in vitro. (Bouyac, M., et al., *J. Virol.* 71(12):9358-65, 1997). Recent studies demonstrate not only that HIV-1 Vif is an RNA binding protein and an integral component of an mRNP complex of viral RNA in the cytoplasm but also that it could be involved in the viral RNA packaging process. (Zhang, H., et al., *J. Virol.* 74; 8252-8261, 2000). In contrast to interactions with NCp7 via its C-terminus, Vif binds to RNA via its N-terminus. When RNA is mixed with Vif or Gag separately, more RNA binds to Vif than to Gag; in contrast, when Vif protein is mixed together with RNA and NCp7, RNA only binds to Gag. (Zhang, H., et al., *J. Virol.* 74; 8252-8261, 2000). This "displacement" may be due to various mechanisms; however, as the domains for Vif multimerization and for Vif-NCp7 binding are quite close in location or possibly overlap, it is possible that the interaction between Vif and Gag, as well as the interactions between Vif, RNA, and Gag, is regulated by Vif multimerization.

In summary, Vif proteins possess a strong tendency to self-associate, forming dimers and multimers. The domain affecting self-association is located at the C-terminus of the protein, specifically the $^{161}$PPLP$^{164}$ domain. The PXP motif-containing peptides block the multimerization of Vif through binding to the $^{161}$PPLP$^{164}$ domain of Vif protein. The evidence reveals that a Vif mutant with deletion at amino acid positions 151-164 is unable to rescue the infectivity of vif-defective viruses generated from H9 T-cells, implying that the multimerization of Vif proteins is important for Vif function in the lentivirus life-cycle.

While this invention has been described with a reference to specific embodiments, it will obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A method of identifying a Vif protein antagonist that specifically binds to a multimerization domain of a Vif protein and inhibits Vif protein multimerization, comprising:

a) contacting a Vif protein or fragment thereof comprising a multimerization domain with a test molecule under conditions conducive to binding between the multimerization domain and said test molecule; and b) determining whether the test molecule specifically binds to the multimerization domain within said Vif protein and inhibits said Vif protein multimerization, wherein the multimerization domain comprises the amino acid sequence Pro-Pro-Leu-Pro (SEQ ID NO: 25).

2. The method of claim 1, wherein the multimerization domain comprises the sequence set forth in SEQ ID NO: 1.

3. The method of claim 1, wherein the multimerization domain comprises the sequence set forth in SEQ ID NO: 26, or a sequence comprising 28 amino acids identical to the sequence set forth in SEQ ID NO: 26.

4. The method of claim 1, further comprising measuring the binding affinity between the test molecule and the multimerization domain.

5. The method of claim 1, wherein a plurality of different test molecules are contacted with the multimerization domain.

6. The method of claim 1, wherein the multimerization domain is immobilized on a solid support.

7. The method of claim 6, wherein the solid support is a column or bead.

8. The method of claim 1, wherein the multimerization domain is fused to glutathione S-transferase.

9. The method of claim 1, wherein the multimerization domain is fused to Gal4.

10. The method of claim 1, wherein the test molecule is a component of a phage display library, chemically synthesized library, or in vitro translation library.

11. The method of claim 1, wherein the test molecule is an antibody or an epitope binding fragment thereof.

12. The method of claim 1, wherein the test molecule comprises a peptide having a Vif protein sequence.

13. The method of claim 1, wherein the test molecule comprises the sequence set forth in SEQ ID NO: 25.

14. The method of claim 1, wherein the test molecule comprises the sequence set forth in SEQ ID NO: 1.

15. The method of claim 1, wherein the test molecule comprises the sequence set forth in SEQ ID NO: 26, or a sequence comprising 28 amino acids identical to the sequence set forth in SEQ ID NO: 26.

16. The method of claim 1, wherein the test molecule is selected from an amino acid having the sequence set forth in SEQ ID NO: 9, SEQ ID NO: 11, SEQ ID NO: 13, SEQ ID NO: 21, SEQ ID NO: 22, SEQ ID NO: 23, and SEQ ID NO: 24.

17. The method of claim 1, wherein the test molecule comprises a nonclassical amino acid.

* * * * *